US011728020B2

(12) United States Patent
Adler et al.

(10) Patent No.: US 11,728,020 B2
(45) Date of Patent: *Aug. 15, 2023

(54) METHODS, SYSTEMS AND APPARATUSES FOR MANAGEMENT AND STORAGE

(71) Applicant: Deborah Adler LLC, Tenafly, NJ (US)

(72) Inventors: Deborah Adler, Tenafly, NJ (US); Duane Sawyer, York, PA (US); Michael Wolf, Geneva, IL (US); Joshua Stewart, Brooklyn, NY (US); Yayun Huang, Rego Park, NY (US)

(73) Assignee: Deborah Adler LLC, New York, NY (US)

( * ) Notice: Subject to any disclaimer, the term of this patent is extended or adjusted under 35 U.S.C. 154(b) by 561 days.

This patent is subject to a terminal disclaimer.

(21) Appl. No.: 16/881,754

(22) Filed: May 22, 2020

(65) Prior Publication Data

US 2020/0286609 A1    Sep. 10, 2020

Related U.S. Application Data

(60) Continuation of application No. 15/600,498, filed on May 19, 2017, now Pat. No. 10,706,961, which is a
(Continued)

(51) Int. Cl.
*G06Q 50/00* (2012.01)
*G06Q 90/00* (2006.01)
(Continued)

(52) U.S. Cl.
CPC ............... *G16H 20/13* (2018.01); *A61J 1/03* (2013.01); *A61J 7/04* (2013.01); *G09F 3/02* (2013.01);
(Continued)

(58) Field of Classification Search
CPC ..... G16H 20/13; A61J 1/03; A61J 7/04; A61J 2205/30; G09F 3/02; G09F 3/0289;
(Continued)

(56) References Cited

U.S. PATENT DOCUMENTS 532,093 A    1/1895  Pollard
2,007,685 A    7/1935  Lyle
(Continued)

FOREIGN PATENT DOCUMENTS

CA    2 527 673 A1    12/2004
CA    3068223 A1    2/2011
(Continued)

OTHER PUBLICATIONS

Alastair J.J. Wood, MD, "Simplifying Medication Scheduling: Can We Confuse Patients Less?," 38 page presentation, retrieved on Jul. 19, 2014, from: www.iom.edu/~/media/Files/Activity%20Files/PublicHealth/HealthLiteracy/wood.pdf, In parent U.S. Appl. No. 13/389,991.
(Continued)

*Primary Examiner* — Maroun P Kanaan
(74) *Attorney, Agent, or Firm* — Brandon N. Sklar, Esq.; The Law Office of Brandon N. Sklar

(57) ABSTRACT

The present invention relates to systems, methods, and apparatuses for the management, distribution, dispensing, and administration of consumer products, including over-the-counter and prescription medications through use of a product container labeling system and an optional integrated computer-based or online management system. In certain aspects, the invention relates to a product container comprising a hollow body, a child-resistant cap, and a specialized information label affixed to the hollow body.

30 Claims, 28 Drawing Sheets

Related U.S. Application Data division of application No. 14/272,000, filed on May 7, 2014, now Pat. No. 9,798,861, which is a continuation-in-part of application No. 13/389,991, filed as application No. PCT/US2011/063900 on Dec. 8, 2011, now Pat. No. 9,643,771, said application No. 13/389,991 is a continuation-in-part of application No. PCT/US2010/045388, filed on Aug. 12, 2010.

(60) Provisional application No. 61/422,008, filed on Dec. 10, 2010, provisional application No. 61/233,781, filed on Aug. 13, 2009, provisional application No. 61/233,426, filed on Aug. 12, 2009.

(51) Int. Cl.
| | | |
|---|---|---|
| *G16H 20/13* | (2018.01) | |
| *G09F 3/02* | (2006.01) | |
| *A61J 1/03* | (2023.01) | |
| *A61J 7/04* | (2006.01) | |
| *G09F 3/00* | (2006.01) | |
| *G09F 3/10* | (2006.01) | |
| *G16Z 99/00* | (2019.01) | |

(52) U.S. Cl.
CPC .............. *G09F 3/0289* (2013.01); *G09F 3/10* (2013.01); *G16Z 99/00* (2019.02); *A61J 2205/30* (2013.01); *G09F 2003/0252* (2013.01); *G09F 2003/0272* (2013.01); *G09F 2003/0273* (2013.01)

(58) Field of Classification Search
CPC .............. G09F 3/10; G09F 2003/0252; G09F 2003/0272; G09F 2003/0273; G16Z 99/00
See application file for complete search history.

(56) References Cited

U.S. PATENT DOCUMENTS

| | | | |
|---|---|---|---|
| 4,028,824 | A | 6/1977 | Miller |
| 4,128,954 | A | 12/1978 | White |
| 4,312,523 | A | 1/1982 | Haines |
| 4,318,477 | A | 3/1982 | Kerpe |
| RE30,958 | E | 6/1982 | White |
| 4,727,667 | A | 3/1988 | Ingle |
| 4,730,849 | A | 3/1988 | Siegel |
| 4,732,411 | A | 3/1988 | Siegel |
| 4,766,542 | A | 8/1988 | Pilarczyk |
| 4,799,712 | A | 1/1989 | Biava et al. |
| 4,883,180 | A | 11/1989 | Humphrey et al. |
| 5,031,937 | A | 7/1991 | Nellhaus |
| 5,102,169 | A | 4/1992 | Mayfield |
| 5,207,746 | A | 5/1993 | Jones |
| 5,261,702 | A | 11/1993 | Mayfield |
| 5,342,093 | A | 8/1994 | Weernink |
| D350,691 | S | 9/1994 | Simion |
| 5,495,944 | A | 3/1996 | Lerner |
| 5,642,906 | A | 7/1997 | Foote et al. |
| 5,687,863 | A | 11/1997 | Kusz |
| 5,727,819 | A | 3/1998 | Grooskopf et al. |
| 5,752,723 | A | 5/1998 | Robertson |
| 5,779,072 | A | 7/1998 | Krebs |
| 5,829,789 | A | 11/1998 | Treleaven et al. |
| 5,958,536 | A | 9/1999 | Gelsinger et al. |
| 5,991,731 | A | 11/1999 | Colon et al. |
| 6,014,631 | A | 1/2000 | Teagarden et al. |
| 6,189,936 | B1 | 2/2001 | Erber et al. |
| 6,260,761 | B1 | 7/2001 | Peoples, Jr. |
| 6,263,330 | B1 | 7/2001 | Bessette |
| 6,272,777 | B1 | 8/2001 | Swenson |
| 6,305,377 | B1 | 10/2001 | Portwood et al. |
| 6,352,608 | B1 | 3/2002 | Garden |
| 6,357,798 | B1 | 3/2002 | Chess |
| 6,367,640 | B1 | 4/2002 | Julian |
| 6,402,872 | B1 | 6/2002 | Key |
| 6,432,500 | B1 | 8/2002 | Jones et al. |
| 6,491,995 | B1 | 12/2002 | Schreiner |
| 6,613,410 | B1 | 9/2003 | Sellars |
| 6,637,775 | B1 | 10/2003 | Bernier et al. |
| 6,671,563 | B1 | 12/2003 | Engelson et al. |
| 6,680,098 | B1 | 1/2004 | Aakermann |
| 6,757,898 | B1 | 6/2004 | Ilsen et al. |
| 6,770,345 | B2 | 8/2004 | Sellars |
| 6,802,810 | B2 | 10/2004 | Ciarniello et al. |
| 6,860,513 | B2 | 3/2005 | Kaufman |
| 6,953,207 | B2 | 10/2005 | Raming |
| 6,967,046 | B2 | 11/2005 | Bollinger et al. |
| 6,988,075 | B1 | 1/2006 | Hacker |
| 6,994,249 | B2 | 2/2006 | Peterka et al. |
| 7,039,628 | B2 | 5/2006 | Logan, Jr. |
| 7,076,437 | B1 | 7/2006 | Levy |
| 7,195,689 | B2 | 3/2007 | Adams et al. |
| D540,179 | S | 4/2007 | Adler et al. |
| D540,690 | S | 4/2007 | Adler et al. |
| D542,661 | S | 5/2007 | Adler et al. |
| 7,225,052 | B2 | 5/2007 | Foote et al. |
| D544,789 | S | 6/2007 | Kaufman |
| 7,225,937 | B2 | 6/2007 | Schroeder |
| 7,286,997 | B2 | 10/2007 | Spector et al. |
| 7,311,205 | B2 | 12/2007 | Adler et al. |
| D562,687 | S | 2/2008 | Kaufman |
| 7,395,214 | B2 | 7/2008 | Shillingburg |
| 7,398,999 | B2 | 7/2008 | Kaufman |
| D574,717 | S | 8/2008 | Adler et al. |
| 7,413,082 | B2 | 8/2008 | Adler et al. |
| 7,424,437 | B2 | 9/2008 | Maus et al. |
| 7,426,475 | B1 | 9/2008 | Tangellapally et al. |
| D581,275 | S | 11/2008 | Adler et al. |
| D583,242 | S | 12/2008 | Adler et al. |
| 7,458,177 | B2 | 12/2008 | Sandel et al. |
| 7,464,043 | B1 | 12/2008 | Dussia |
| D594,336 | S | 6/2009 | Adler |
| 7,740,411 | B2 | 6/2010 | Kaufman |
| 7,926,850 | B1 | 4/2011 | Muncy et al. |
| 7,926,851 | B2 | 4/2011 | Kaufman |
| 8,020,702 | B2 | 9/2011 | Strub et al. |
| 8,025,314 | B2 | 9/2011 | Adler |
| 8,037,628 | B2 | 10/2011 | Kaufman |
| 9,643,771 | B2 | 5/2017 | Adler et al. |
| 9,782,327 | B2 | 10/2017 | Miceli et al. |
| 9,798,861 | B2 | 10/2017 | Adler et al. |
| 10,095,997 | B2 | 10/2018 | Adler et al. |
| 10,403,396 | B2 | 9/2019 | Adler et al. |
| 10,706,961 | B2 | 7/2020 | Adler et al. |
| 2001/0001144 | A1 | 5/2001 | Kapp |
| 2002/0171238 | A1 | 11/2002 | Kozlowski et al. |
| 2002/0184051 | A1 | 12/2002 | Yu et al. |
| 2003/0047937 | A1 | 3/2003 | Chaduc et al. |
| 2003/0111837 | A1 | 6/2003 | Foote et al. |
| 2003/0112466 | A1 | 6/2003 | Leonardi |
| 2003/0177033 | A1 | 9/2003 | Park et al. |
| 2003/0189732 | A1 | 10/2003 | Bean et al. |
| 2003/0193181 | A1 | 10/2003 | Hung |
| 2003/0193185 | A1 | 10/2003 | Valley et al. |
| 2003/0205897 | A1 | 11/2003 | Kaufman |
| 2003/0214129 | A1 | 11/2003 | Adler |
| 2003/0225595 | A1 | 12/2003 | Helmus et al. |
| 2004/0009347 | A1 | 1/2004 | Bolnick et al. |
| 2004/0075272 | A1 | 4/2004 | Kaufman |
| 2004/0153339 | A1 | 8/2004 | Hetzel |
| 2004/0169000 | A1 | 9/2004 | Ramsey |
| 2004/0181982 | A1 | 9/2004 | Sandel et al. |
| 2004/0193454 | A1 | 9/2004 | Foote et al. |
| 2004/0199404 | A1 | 10/2004 | Ripperger et al. |
| 2004/0243434 | A1 | 12/2004 | Peterka et al. |
| 2004/0243445 | A1 | 12/2004 | Keene |
| 2004/0247812 | A1 | 12/2004 | Milliorn et al. |
| 2004/0251165 | A1 | 12/2004 | Girzaitis |
| 2005/0019518 | A1 | 1/2005 | Bollinger et al. |
| 2005/0038558 | A1 | 2/2005 | Keene |
| 2005/0040642 | A1 | 2/2005 | Jiang |
| 2005/0056203 | A1* | 3/2005 | Giewercer ................ G09F 3/00 116/308 |

(56) References Cited

U.S. PATENT DOCUMENTS

| | | |
|---|---|---|
| 2005/0140135 A1 | 6/2005 | Miller et al. |
| 2005/0171815 A1 | 8/2005 | Vanderveen |
| 2005/0268505 A1 | 12/2005 | Sandel et al. |
| 2006/0029766 A1 | 2/2006 | Bolnick et al. |
| 2006/0078701 A1 | 4/2006 | Glasier |
| 2006/0144919 A1 | 7/2006 | Tong |
| 2006/0163103 A1 | 7/2006 | Adler et al. |
| 2006/0163110 A1 | 7/2006 | Adler et al. |
| 2006/0163869 A1 | 7/2006 | Adler et al. |
| 2006/0197336 A1 | 9/2006 | Londino |
| 2007/0029788 A1 | 2/2007 | Adler |
| 2007/0034103 A1 | 2/2007 | Kaufman |
| 2007/0095850 A1 | 5/2007 | Meyer |
| 2007/0164096 A1 | 7/2007 | Banfield et al. |
| 2007/0172429 A1 | 7/2007 | Gao et al. |
| 2007/0204497 A1 | 9/2007 | de la Huerga |
| 2007/0214018 A1 | 9/2007 | Claud, III |
| 2007/0250341 A1 | 10/2007 | Howe et al. |
| 2007/0250346 A1 | 10/2007 | Luciano, Jr. et al. |
| 2007/0252378 A1 | 11/2007 | Chambers |
| 2007/0267430 A1 | 11/2007 | Luciano, Jr. et al. |
| 2007/0270998 A1 | 11/2007 | Luciano, Jr. et al. |
| 2008/0015897 A1 | 1/2008 | Moradi et al. |
| 2008/0017602 A1 | 1/2008 | Adler et al. |
| 2008/0035659 A1 | 2/2008 | Ricker et al. |
| 2008/0042423 A1 | 2/2008 | Roberts et al. |
| 2008/0046294 A1 | 2/2008 | Fiedotin et al. |
| 2008/0052129 A1 | 2/2008 | Beraja et al. |
| 2008/0056556 A1 | 3/2008 | Eller et al. |
| 2008/0071572 A1 | 3/2008 | Ahmed |
| 2008/0086337 A1 | 4/2008 | Soon-Shiong |
| 2008/0086339 A1 | 4/2008 | Jung et al. |
| 2008/0091468 A1 | 4/2008 | Heidenreich et al. |
| 2008/0097787 A1 | 4/2008 | Palazzolo et al. |
| 2008/0097918 A1 | 4/2008 | Dicks et al. |
| 2008/0099367 A1 | 5/2008 | Niemiec et al. |
| 2008/0103827 A1 | 5/2008 | Niemiec et al. |
| 2008/0126135 A1 | 5/2008 | Woo |
| 2008/0140449 A1 | 6/2008 | Hayes |
| 2008/0150275 A1 | 6/2008 | Raistrick |
| 2008/0154643 A1 | 6/2008 | Leon |
| 2008/0162181 A1 | 7/2008 | Ben-Haim et al. |
| 2008/0197619 A1 | 8/2008 | Tussey |
| 2008/0201173 A1 | 8/2008 | Takehara et al. |
| 2008/0215374 A1 | 9/2008 | Craft |
| 2008/0228519 A1 | 9/2008 | Leon |
| 2008/0228524 A1 | 9/2008 | Brown |
| 2008/0235050 A1 | 9/2008 | Hallberg |
| 2008/0235059 A1 | 9/2008 | Gonzalvo |
| 2008/0257777 A1 | 10/2008 | Miceli et al. |
| 2008/0262868 A1 | 10/2008 | Malolepszy |
| 2008/0262930 A1 | 10/2008 | Miceli et al. |
| 2008/0276008 A1 | 11/2008 | Leon |
| 2008/0287746 A1 | 11/2008 | Reisman |
| 2008/0288287 A1 | 11/2008 | Stanners et al. |
| 2008/0294462 A1 | 11/2008 | Nuhaan et al. |
| 2008/0301982 A1 | 12/2008 | Kaufman |
| 2008/0303264 A1 | 12/2008 | Kaufman |
| 2008/0312957 A1 | 12/2008 | Luciano, Jr. et al. |
| 2008/0319784 A1 | 12/2008 | Cordero |
| 2009/0012373 A1 | 1/2009 | Raij et al. |
| 2009/0012820 A1 | 1/2009 | Bishop et al. |
| 2009/0019552 A1 | 1/2009 | McLaughlin et al. |
| 2009/0024416 A1 | 1/2009 | McLaughlin et al. |
| 2009/0024417 A1 | 1/2009 | Marks et al. |
| 2009/0030719 A1 | 1/2009 | Nadas et al. |
| 2009/0030725 A1 | 1/2009 | Palazzolo et al. |
| 2009/0140513 A1 | 6/2009 | Priebe et al. |
| 2010/0042430 A1* | 2/2010 | Bartfeld ............... G06Q 99/00 705/2 |
| 2011/0000170 A1 | 1/2011 | Burg et al. |
| 2011/0184753 A1 | 7/2011 | Tripoli et al. |
| 2013/0341329 A1 | 12/2013 | Adler et al. |
| 2014/0156298 A1 | 6/2014 | Crawford et al. |
| 2014/0195042 A1 | 7/2014 | Adler |
| 2014/0246349 A1 | 9/2014 | Adler et al. |
| 2014/0257843 A1 | 9/2014 | Adler et al. |
| 2015/0352009 A1 | 12/2015 | Miller |
| 2017/0039342 A1 | 2/2017 | Nichols et al. |
| 2019/0080793 A1 | 3/2019 | Adler et al. |

FOREIGN PATENT DOCUMENTS

| | | |
|---|---|---|
| CA | 3086500 A1 | 6/2012 |
| CA | 2769851 | 3/2020 |
| CA | 2819131 | 9/2020 |
| CN | 1911739 A | 2/2007 |
| CN | 1911740 A | 2/2007 |
| DE | 102005056037 A1 | 6/2007 |
| EP | 0 441 023 A2 | 8/1991 |
| EP | 1 882 635 A2 | 1/2008 |
| GB | 2006713 A | 5/1979 |
| GB | 2 277 075 A | 10/1994 |
| GB | 2 380 467 A | 4/2003 |
| JP | 10-297640 A | 11/1998 |
| JP | 2003-108002 A | 4/2003 |
| JP | 2006-68175 A | 3/2006 |
| WO | WO 01/68454 A2 | 9/2001 |
| WO | WO 02/29664 A1 | 4/2002 |
| WO | WO 2002/094579 A1 | 11/2002 |
| WO | WO 03/098275 A2 | 11/2003 |
| WO | WO 2004/084159 A2 | 9/2004 |
| WO | WO 2004/109626 A2 | 12/2004 |
| WO | WO 2005/020195 A2 | 3/2005 |
| WO | WO 2006/049937 A2 | 5/2006 |
| WO | WO 2006/080945 A1 | 8/2006 |
| WO | WO 2007/074394 A3 | 7/2007 |
| WO | WO 2007/084159 A2 | 7/2007 |
| WO | WO 2007/127359 A3 | 11/2007 |
| WO | WO 2011/019967 A1 | 2/2011 |
| WO | WO 2012/078840 | 4/2012 |

OTHER PUBLICATIONS

"Aligning medication containers label—Google Search," 2 pages, retrieved on Apr. 15, 2019, from www.google.com, In parent U.S. Appl. No. 15/600,498.

"Aligning medication containers label instructions—Google Search," 2 pages, retrieved on Apr. 15, 2019, from www.google.com, In parent U.S. Appl. No. 15/600,498.

Bailey et al., "A Universal Medication Schedule to Promote Patient Understanding and Use," 17 pages, retrieved on Dec. 16, 2013, from: www.bumc.bu.edu/healthliteracyconverence/files/2009/10/bailey-2009_1.pdf, In parent U.S. Appl. No. 13/389,991.

Canadian Examiner's Report dated Apr. 4, 2017, issued in CA 2,769,851, In parent U.S. Appl. No. 15/600,498.

Canadian Examiner's Report dated Feb. 24, 2016, issued in CA 2,769,851, In parent U.S. Appl. No. 15/600,498.

"ConXus Workplace Wellnes Platform | PDHI," 1 page, retrieved on Oct. 26, 2012, from www.pdhi.com, In parent U.S. Appl. No. 13/389,991.

Gross, "Microsoft launches online e-health service," 3 pages, retrieved on Feb. 1, 2009, from www.computerworld.com, In parent U.S. Appl. No. 13/389,991.

Hernandez, "Standardizing Medication Labels: Confusing Patients Less, Workshop Summary," (2008), In parent U.S. Appl. No. 15/600,498.

International Search Report, International Application No. PCT/US2010/045388 (published as WO 2011/019967) (dated Jan. 18, 2011), In parent U.S. Appl. No. 13/389,991.

International Search Report dated Apr. 19, 2012, in International Patent Application No. PCT/US2011/063900, In parent U.S. Appl. No. 13/389,991.

Kripalani et al., "Development of an Illustrated Medication Schedule as a Low-Literacy Patient Education Tool," *Patient Education and Counseling* 66:368-377 (2007), In parent U.S. Appl. No. 15/600,498.

Kusserow, Medication Regimens: Causes of Noncompliance, Office of Inspector General—OEI-04-89-891 21. 38 pgs. (1990) <https://oig.hhs.gov/oei/reports/oei-04-89-89121.pdf>, In parent U.S. Appl. No. 13/389,991.

(56) References Cited

OTHER PUBLICATIONS

"MyMedicalRecords.com User Guide," 15 pages, dated May 31, 2007, In parent U.S. Appl. No. 13/389,991.
"NoMoreClipboard.com—Your Secure Personal Health Record," 5 pages, retrieved on Feb. 1, 2009, from www.nomoreclipboard.com, In parent U.S. Appl. No. 13/389,991.
"PersonalMD.Com—Your Lifeline Online," 9 pages, retrieved on Feb. 1, 2009, from www.personalmd.com, In parent U.S. Appl. No. 13/389,991.
Third-Party Submission Under 37 CFR 1.290 and Concise Description of Relevance filed Nov. 1, 2019, in U.S. Appl. No. 16/350,213, In parent U.S. Appl. No. 15/600,498.
Vascellaro et al., "Google, IBM Promote Online Health Records," *The Wall Street Journal*, Feb. 5, 2009 (1 page), In parent U.S. Appl. No. 13/389,991.
Katz et al., "Use of pictorial aids in medication instructions: A review of the literature," *Am JHealth-Syst Pharm* 63:2391-2397 (2006).

\* cited by examiner

TAKE
TAKE 1 TABLET
BY MOUTH
AT BEDTIME.

ADVICE
DRINK PLENTY OF WATER
WHILE TAKING THIS
MEDICATION.

PROVIDER INFO
DOCTOR:
PHONE:

PATIENT INFO
ERIC SILVERMAN
60 EAST 8TH ST #5E
NYC 10003
DRUG INFO
DRUG: PRAVASTATIN
SODIUM
40MG
GENERIC:
DESCRIPTION: WHITE
TABLET
USES: CHOLECTEROL
PARMACY INFO
RX#006619325
REFILLS: 02 THRU
05/28/09
QTY: 30 PILLS
QTY: 300
DRUG EXP: 05/28/09
DATE FILLED: 05/25/08

RX INFO AND WARNINGS

① CONSULT YOUR DOCTOR OR PHARMACIST
BEFORE BREASTFEEDING.
② TALK TO YOUR DOCTOR ABOUT ALL
OTHER MEDICINES YOU MAY BE TAKING.
③ LIMIT THE AMOUNT OF SALT IN YOUR DIET.

VISIT ADLERRX.COM TO
MANAGE YOUR
MEDICATIONS

PHARMACY
1525 MAIN ST. YORKVILLE
NY 10456
TEL: 212-XXX-XXXX

510a — PATIENT INFO / ERIC SILVERMAN / 60 EAST 6TH ST #5E / NYC 10003 / DRUG INFO / DRUG: PRAVASTATIN SODIUM / 40MG / GENERIC: / DESCRIPTION: WHITE TABLET / USES: CHOLESTEROL / PHARMACY INFO / RX#40088819325 / REFILLS: 02 THRU 05/28/09 / QTY: 30 PILLS / DATE FILLED: 08/28/08 / DRUG EXP: 08/28/09

510b — TAKE / TAKE 1 TABLET / BY MOUTH / AT BEDTIME. / ADVICE / DRINK PLENTY OF WATER WHILE TAKING THIS MEDICATION. / PROVIDER INFO / DOCTOR: / PHONE:

510c — ERIC / AM / NOON / EVE / BED / WWW.ADLERRX.COM

510d — PRAVASTATIN SODIUM 40MG

510e:
- 510e-1: RX INFO AND WARNINGS: / ① CONSULT YOUR DOCTOR OR PHARMACIST BEFORE BREASTFEEDING. / ② TALK TO YOUR DOCTOR ABOUT ALL OTHER MEDICINES YOU MAY BE TAKING. / ③ LIMIT THE AMOUNT OF SALT IN YOUR DIET. / PHARMACY / 1525 MAIN ST. YORKVILLE / NY 10458 / TEL: 212-XXX-XXXX
- 510e-2: VISIT ADLERRX.COM TO MANAGE YOUR MEDICATIONS

FIG. 5B

512a — TAKE / TAKE 1 TABLET / BY MOUTH / AT BEDTIME. / ADVICE / DRINK PLENTY OF WATER WHILE TAKING THIS MEDICATION. / OPEN HERE FOR MORE INFO AND WARNINGS.

512b — DRUG INFO / PRAVASTATIN SODIUM / 40MG / PREPARED FOR / ERIC SILVERMAN / 60 EAST 6TH ST #5E / NYC 10003 / PHARMACY INFO / RX# 29419325 / PHARMACY / 1525 MAIN ST. YORKVILLE / NY 10458 / TEL: 212-XXX-XXXX

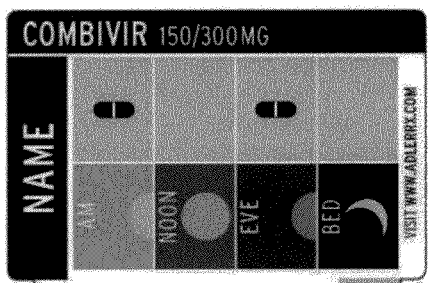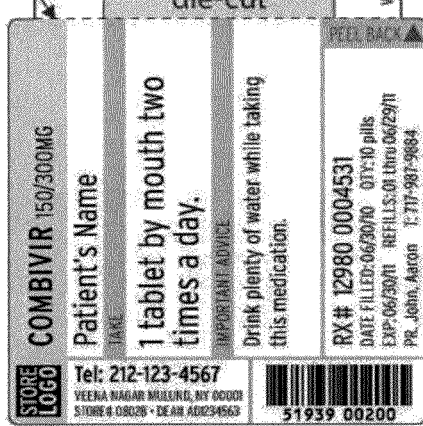
FIG. 7A

ADLER RX

Site Map

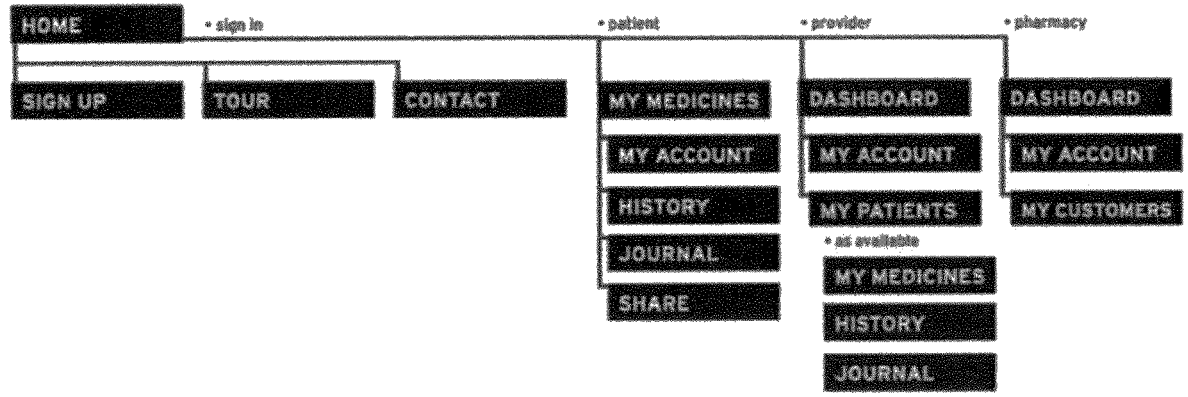

Content Outline

Home:
- logo
- tagline
- exposed sign in form
- explanation of system and images of parts
- why Adler Rx copy
- link to Tour
- link to Sign Up page

Sign up
- email
- name
- zip
- password
- pharmacy code (or some other system to control who can sign up)
- select bullet points on why Adler Rx
- optional: add alerts and history at the time of signing up

Tour
- step by step of the process and capabilities of the system and site
- could be multiple pages, video or both

Contact

My Medicines
- list of all meds
- schedule of meds
- alerts opt in
- side effects
- emergency what to do
- alerts for upcoming refills

My Account
- user name and password settings
- time zone
- age
- sex
- alert devices: email, phone, text

History
- medical history
- medications taken

Journal
- entries for each doctor visit/side effect/question
- Blood pressure/blood sugar/weight etc.

Share (By patient invitation only)
- list of people sharing my info
- what info to share on a per person basis

FIG. 8I

METHODS, SYSTEMS AND APPARATUSES FOR MANAGEMENT AND STORAGE

RELATED APPLICATIONS

This application is a continuation of U.S. patent application Ser. No. 15/600,498, filed May 19, 2017, which is a division of U.S. patent application Ser. No. 14/272,000, filed May 7, 2014, now U.S. Pat. No. 9,798,861, which is a continuation-in-part of U.S. patent application Ser. No. 13/389,991, filed Sep. 11, 2013, now U.S. Pat. No. 9,643,771, which is a national stage under 35 U.S.C. § 371 of International Application No. PCT/US2011/063900, filed Dec. 8, 2011, wherein International Application No. PCT/US2011/063900 claims the benefit of U.S. Provisional Application No. 61/422,008, filed Dec. 10, 2010, and is a continuation-in-part application of International Application No. PCT/US2010/45388, filed Aug. 12, 2010, which claims the benefit of U.S. Provisional Application No. 61/233,426, filed Aug. 12, 2009, and U.S. Provisional Application No. 61/233,781, filed Aug. 13, 2009, the contents of each of which are herein incorporated by reference in their entireties.

FIELD OF THE INVENTION

The present invention relates generally to management and storage, particularly management and storage of consumer products including medication and other regulated consumables.

BACKGROUND OF THE INVENTION

Studies consistently show that patients have limited "health literacy." In other words, patients, generally speaking, have limited understanding of the role they should play in their own health care. Limited patient health literacy results in limited use of preventive services, delayed diagnoses, lack of understanding of medical conditions, poor self-management skills, and failure to adhere to medical instructions. One specific aspect of patient health illiteracy is unintentional non-adherence to a medication regimen; studies have shown that half of patients misunderstand and demonstrate misuse of prescribed medications and that patients unnecessarily overcomplicate multi-drug regimens. Patients' misunderstanding of medication regimens, coupled with greater regimen complexity, results in less effective treatment, worse clinical outcomes, increased risk of hospitalization, poor physical and mental health, increased mortality risk, and greater healthcare costs. Some studies have shown these costs to range between $106 and $223 billion per year. What is needed is a comprehensive system enabling patients, physicians and pharmacists to more effectively communicate, and for patients to gain a greater understanding of their own health care and medication management.

BRIEF SUMMARY OF THE INVENTION

The present disclosure is best understood with reference to the claims, the entire specification, and the drawings submitted herewith, which describe the systems, methods, and apparatuses of the present disclosure in greater detail. The summary is merely intended to convey aspects of illustrative embodiments.

The present disclosure relates to systems, methods, and apparatuses for the management, distribution, dispensing, and administration of consumer products, such as over-the-counter and prescription medications, through use of a product container labeling system and an optional integrated computer-based or online management system.

In certain aspects, the invention relates to a product container, e.g., medication container, comprising a hollow body, a child-resistant cap, and a specialized information label affixed to the hollow body. In certain embodiments, the hollow body may have a squared form that has a rectangular longitudinal shape and a rectangular or square cross-section, with one corner cut across. In other embodiments, the hollow body may have a circular or triangular cross-section.

In certain embodiments, the specialized information label may be configured such that, upon being affixed to the hollow body, part of the hollow body is visible, such that that contained product, e.g., medication, is easily visible though the label. In addition, in certain embodiments, the label may provide extra space for relevant information by providing fold-out panels.

In certain aspects, information printed on the specialized label may be correlated or linked with a computerized or online management system, such as an interactive website to keep, e.g., users, distributors, manufactures, patients, pharmacists, physicians and other interested parties organized and informed with respect to user's activities, e.g., all of a patient's prescribed and over-the-counter medications.

Additional objects, advantages and novel features of this invention will be set forth in part in the detailed description that follows, and in part will become apparent to those skilled in the art upon examination of the following description, or may be learned by practicing the invention.

BRIEF DESCRIPTION OF THE DRAWINGS

In the accompanying drawings that form a part of the specification and are to be read in conjunction therewith, the present invention is illustrated by way of example and not limitation, with like reference numerals referring to like elements, wherein:

FIG. 4 is a rear and left side view of a product container with a specialized label attached and folded out according to one embodiment.

FIGS. 5A-5B illustrate front and rear views of a label detached from a product container and folded out according to embodiments.

FIGS. 7A-7E illustrate a front view of an alternative label in a flat, open position (detached from a container, 7A), a folded in, closed position (detached from a container, 7B), a partially opened position (detached from a container, 7C), a folded out position (detached from a container, 7D), and full views of closed labels attached to exemplary round containers (7E), according to an embodiment.

Figure 8A:
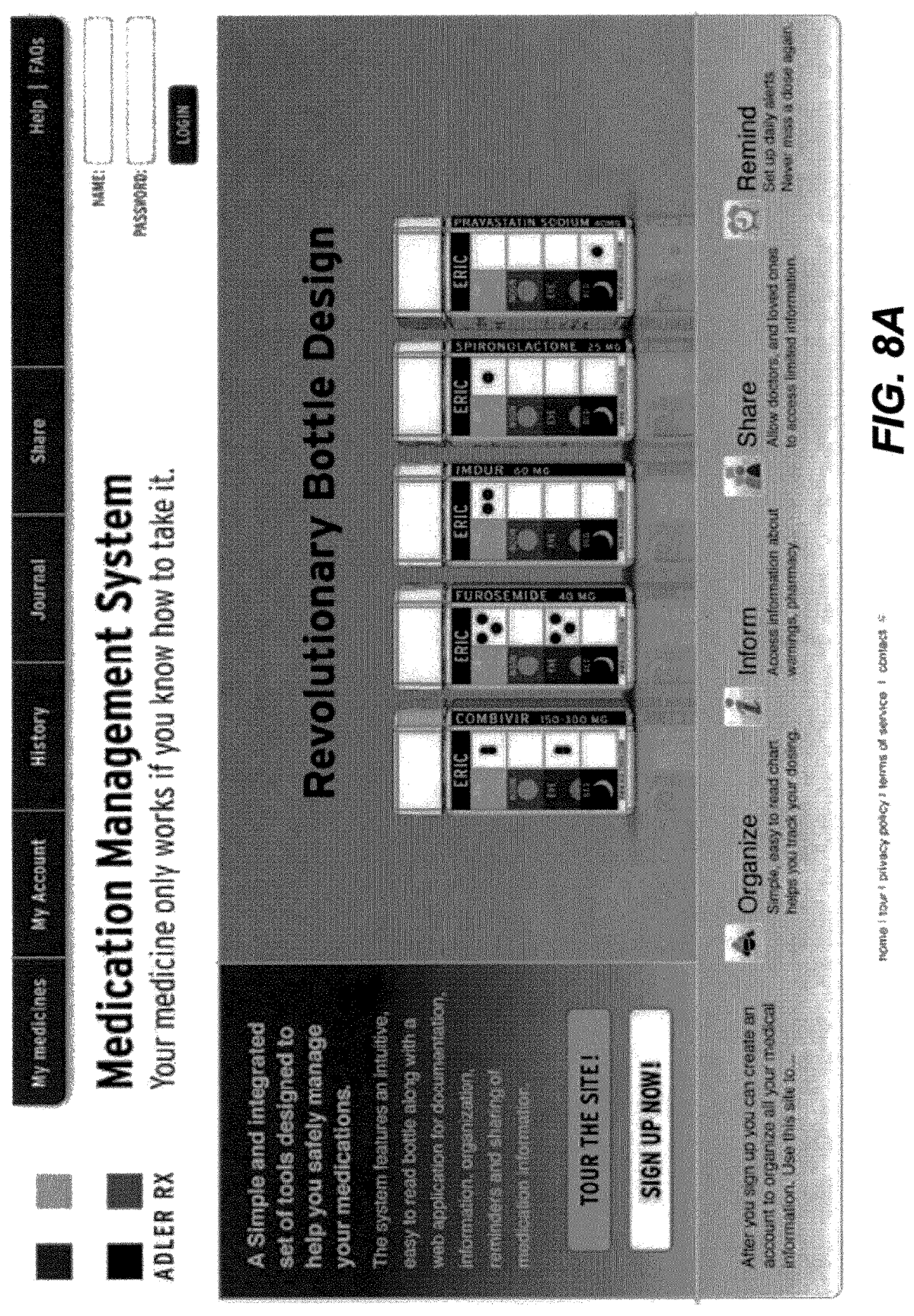
Figure 8C:
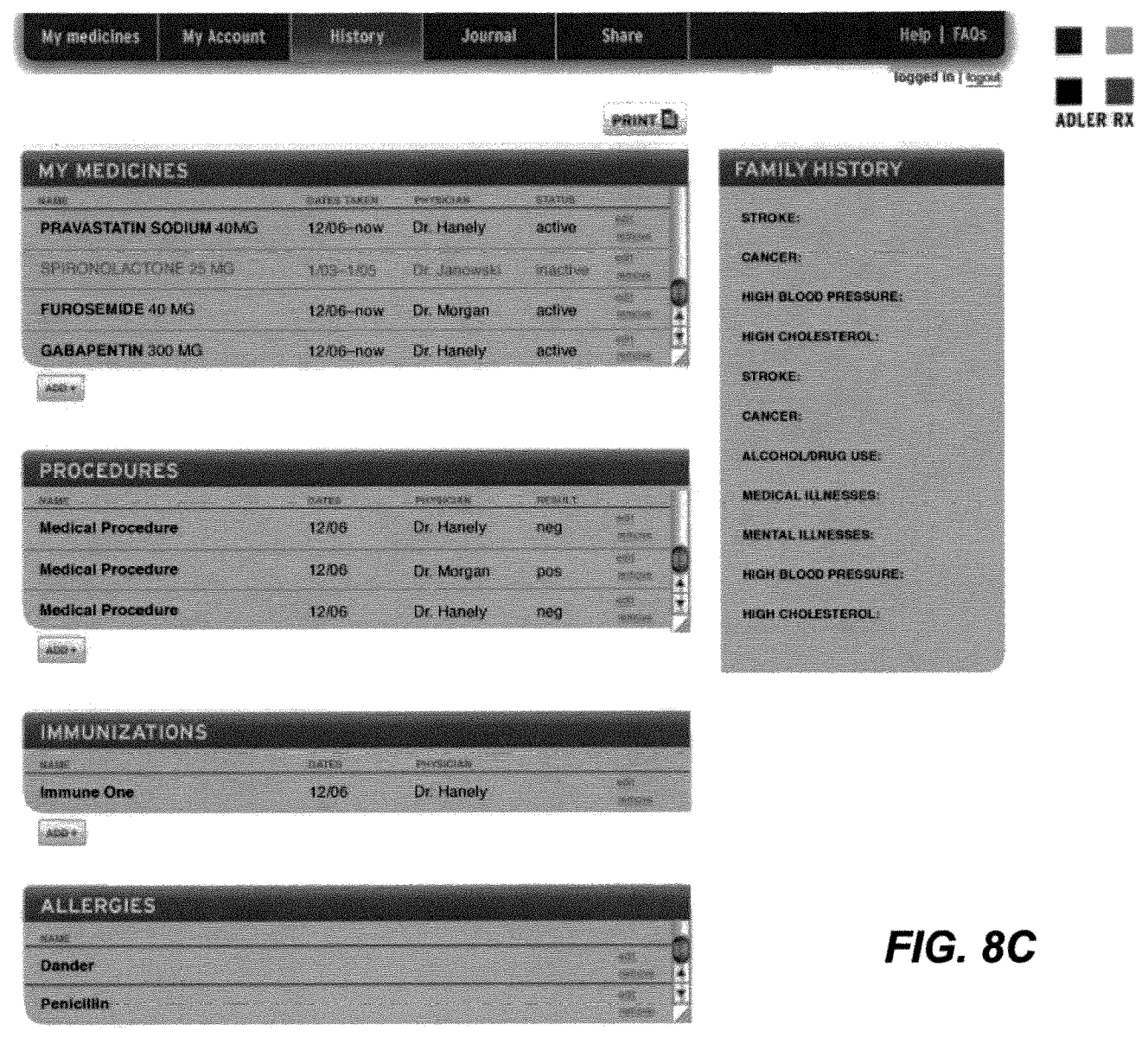
Figure 8E:
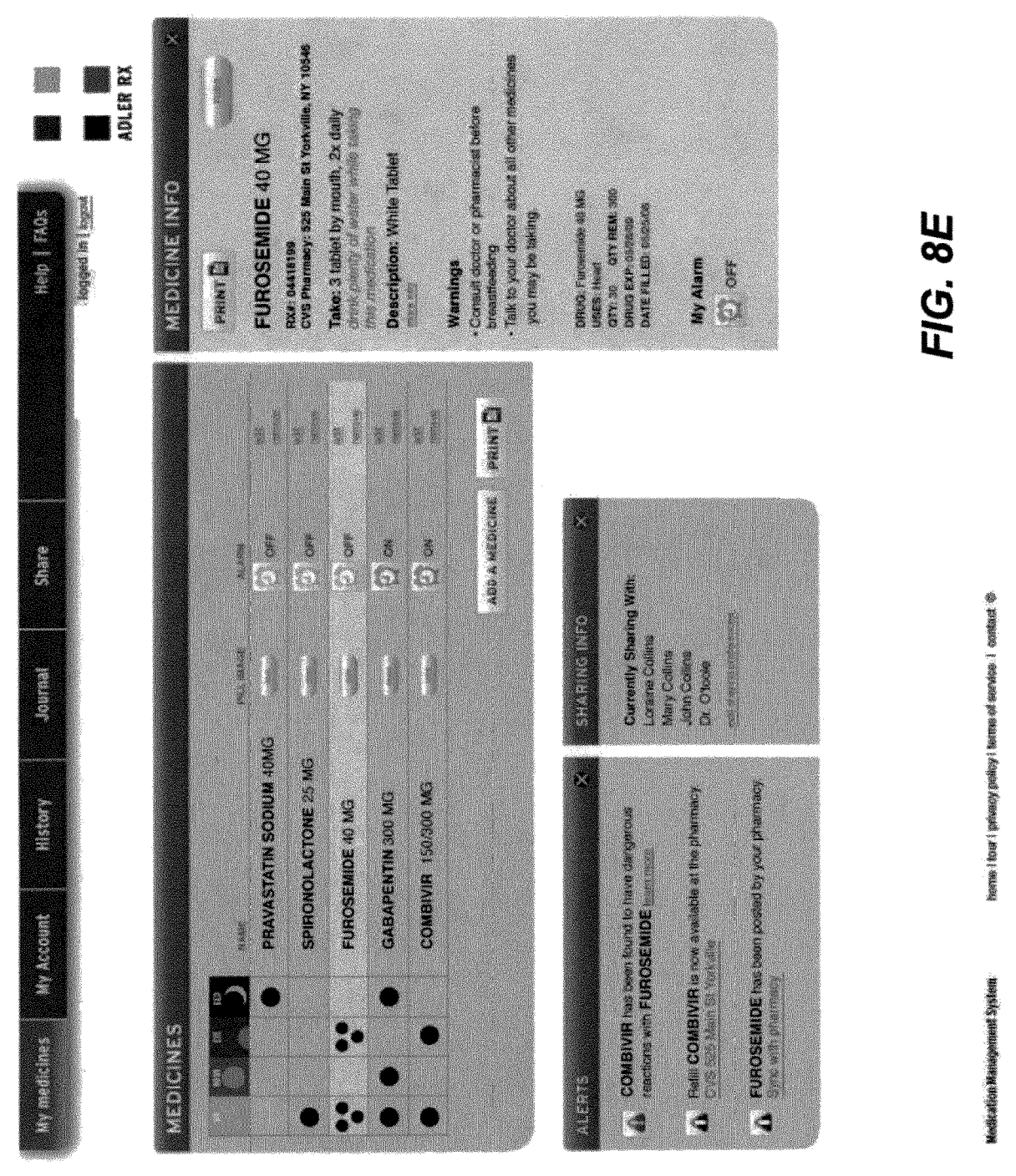
Figure 8F:
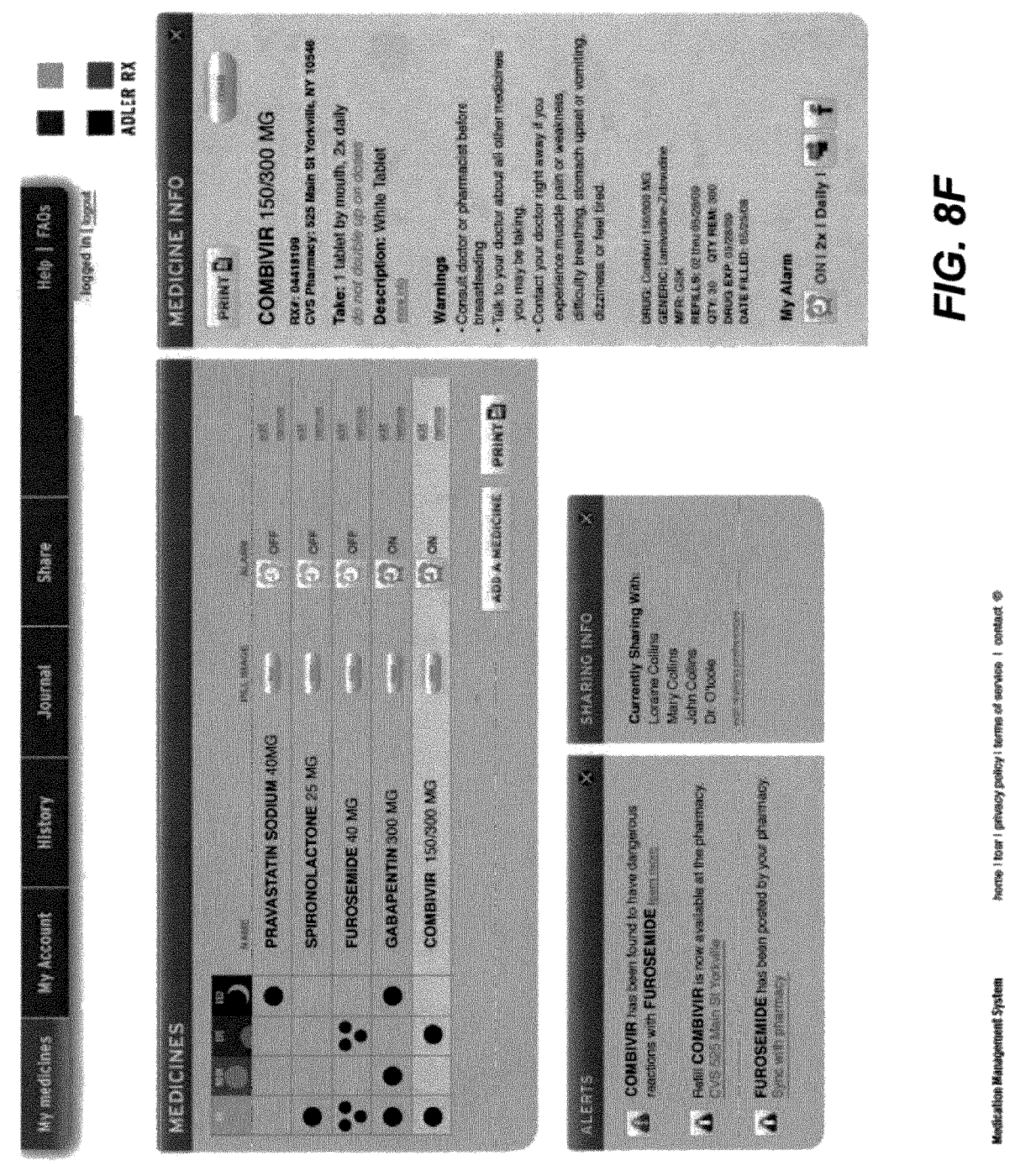
Figure 8H:
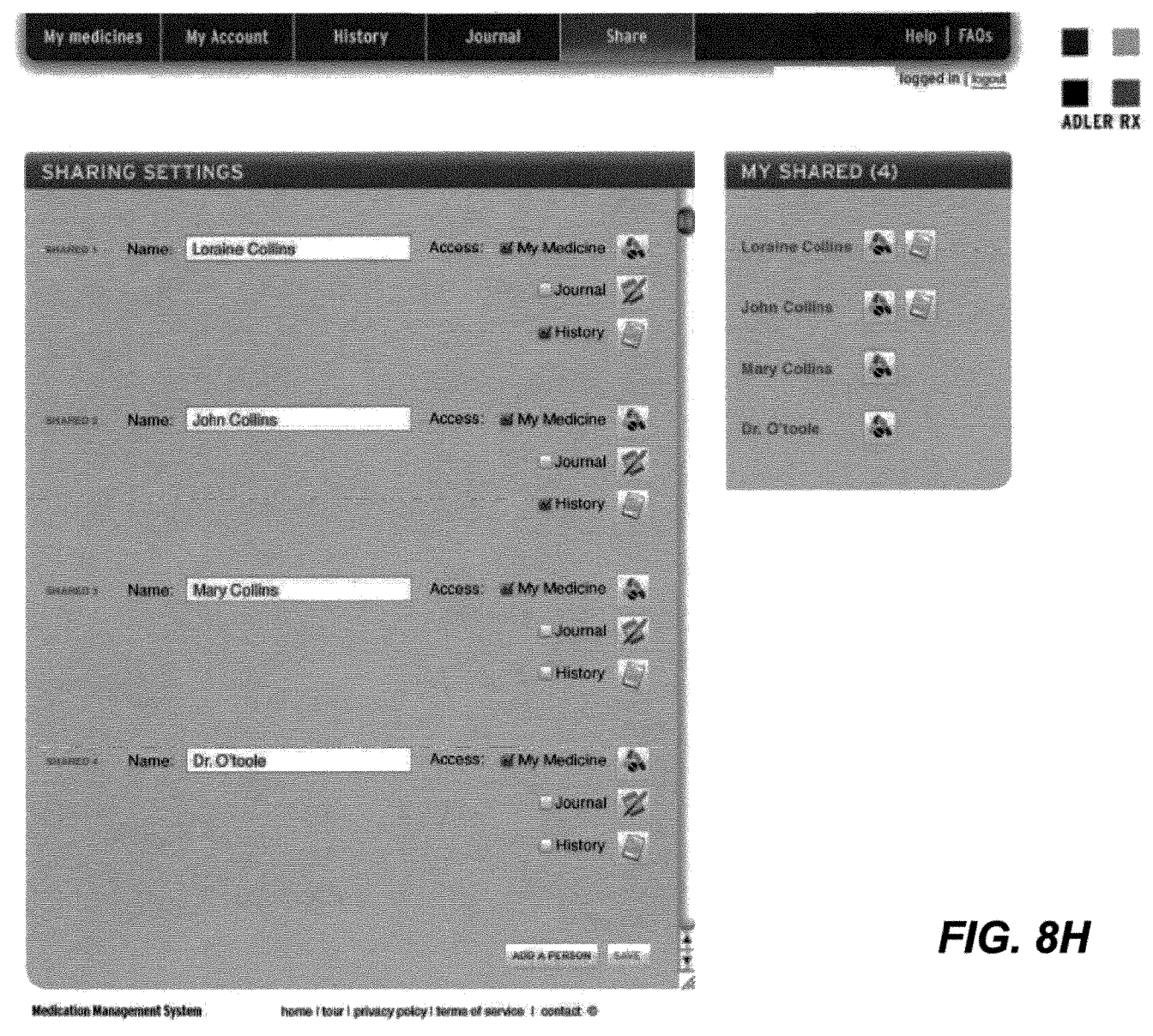

FIGS. 8A-8I describe and illustrate an exemplary interactive medication management system according to an embodiment.

DETAILED DESCRIPTION

In the following detailed description, numerous specific details are set forth in order to provide a thorough understanding of embodiments of the disclosure. In other instances, well known structures, interfaces, and processes have not been shown in detail, as they are understood by those of skill in the art. It is intended that no part of this specification be construed to effect a disavowal of any part of the full scope of the disclosure.

The present invention relates to systems, methods, and apparatuses for the management, distribution, dispensing, and administration of consumer products, such as over-the-counter and prescription medications through use of a product container labeling system and an optional integrated computer-based or online management system. In certain embodiments, the invention relates to systems, methods, and apparatuses for use in connection with over-the-counter and prescription medications or other regulated consumer products. However, the invention is not so limited, and may be used in connection with any general consumer product, container and labeling system, etc., as may be understood by one of skill in the art. For instance, the specialized information label systems described herein may be used in connection with any suitable consumer product container, e.g., re-usable water or drink bottle, food container, drink container, etc. As will be recognized, the specialized information label systems of the invention may be used to provide required labeling, contents, ingredients, instructions, warnings, etc., for any consumer product, and can be configured to accommodate any consumer product packaging.

In certain aspects, the invention relates to a product container comprising a hollow body, a child-resistant cap, and a specialized information label affixed to the hollow body. In certain embodiments, the hollow body may have a squared form that has a rectangular longitudinal shape and a rectangular or square cross-section, optionally with one corner cut across. In other embodiments, the hollow body may have a rounded form, optionally with one corner cut across.

More particularly, the cap and the neck of the hollow body provide a unique child-resistant mechanism. In certain embodiments, the mechanism is tabbed, requiring a user to press the corners of the hollow body instead of the sides. This closure provides the spring mechanism required to reposition the tab after it has been reassembled onto the container.

Figure 1:
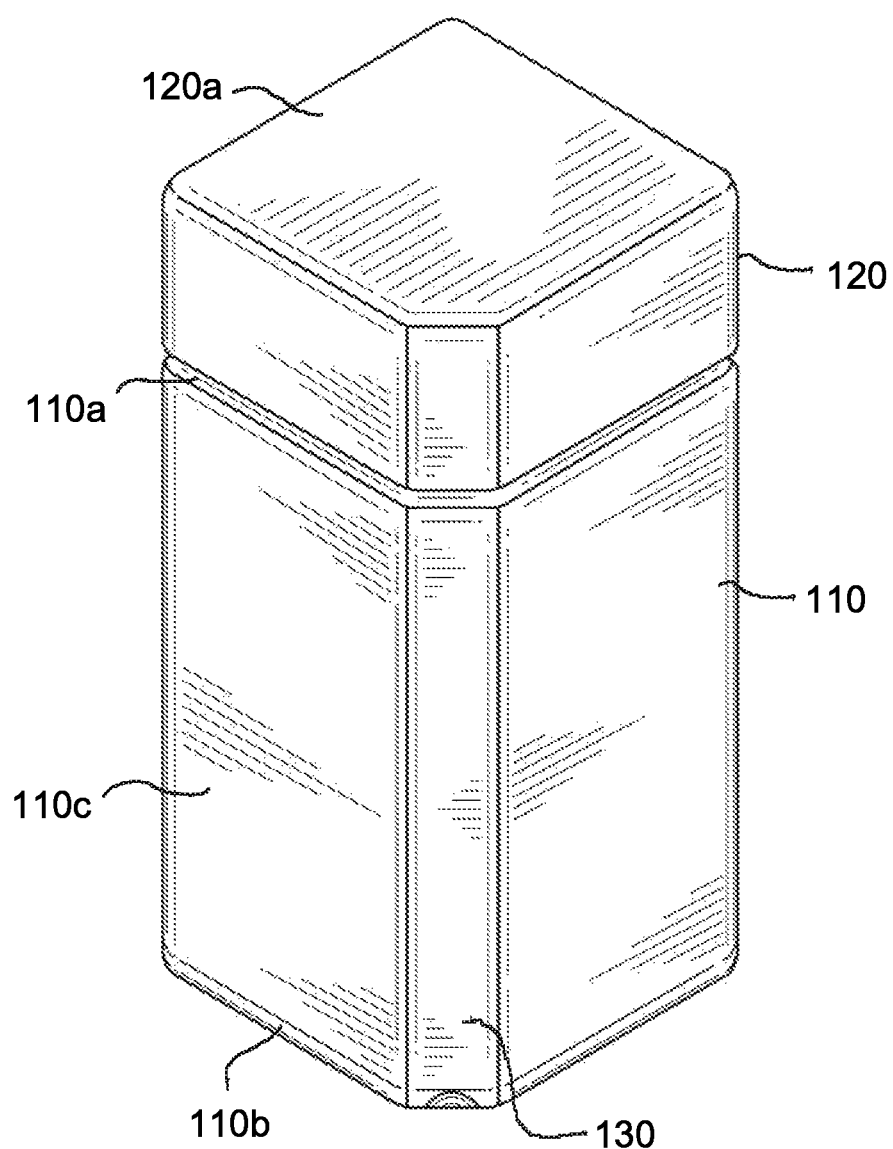
FIG. 1 is a top right perspective view of a squared product container with the cap attached according to one embodiment.

In one embodiment, as illustrated in FIG. 1, the hollow body 110 of the pharmaceutical container 100 has a squared form. In one particular embodiment, the squared form may have a rectangular longitudinal shape. In an alternative embodiment, the squared form may have a square cross-section shape. However, the disclosure is not so limited and alternative forms of the hollow body are within the scope of the present disclosure, e.g., round, triangular, etc.

With reference to FIG. 1, hollow body 110 and cap 120 including one or more flat surfaces 130 may be preferred, as opposed to hollow forms including solely curved surface (e.g., a round bottle). However, any suitable hollow form may be used. In certain embodiments, the hollow body may have a square form, triangular form, round form, etc., except that one or more corners, edges, or select portions of the cross-sectional form is optionally cut off at an angle to create a flat side(s) 130 (the "Flat," see, e.g., FIG. 1). In certain aspects, the Flat 130 may be used to accommodate a unique label feature, printed information, organizing information, etc.

In certain embodiments, the hollow body may be round in form with one or more portions of the cross-sectional form optionally cut off at an angle to create one or more flat side(s). In other embodiments, the hollow body may be triangular in form with one or more corners of the cross-sectional form cut off at an angle to create one or more flat side(s). In yet other embodiments, the hollow body may be square or rectangular in form with one or more edges or corners cut off at an angle to create one or more flat side(s).

Figure 2:
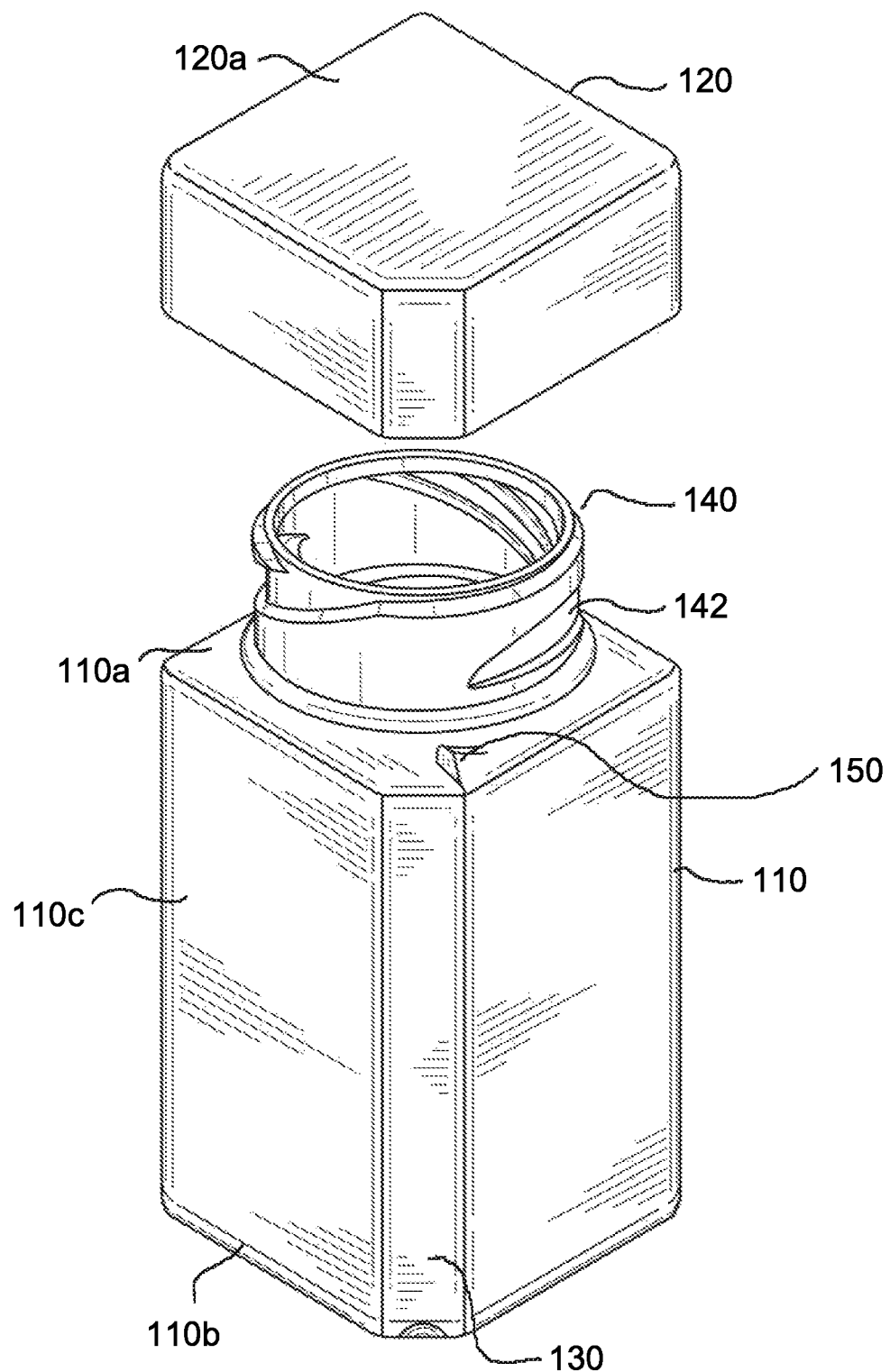
FIG. 2 is a top right perspective view of a product container with the cap detached according to one embodiment.

FIG. 2 illustrates product container 100 with cap 120 in a detached position from hollow body 110, exposing a container neck 140 and threads or locking protrusions 142. FIG. 3 shows the inside of the cap 120. The threads or locking protrusions 142 of the product container 100 correspond to the threads or locking protrusions 144 of cap socket 146. In one embodiment, multi-lead threads 142 of various sizes and configuration on the neck 140 of the hollow body 110, for which the bottle cap 120 is correspondingly grooved 144, ensure that the closure can be applied in only one position. Again, in certain embodiments, a locking mechanism may be including, such as tab 150 on hollow body 110 and corresponding locking tab 152 on cap 120, requiring a user to press the corners of the hollow body 110 to disengage locking tab 152. This closure provides the spring mechanism required to reposition the tab after it has been reassembled onto the container.

Figure 3A:
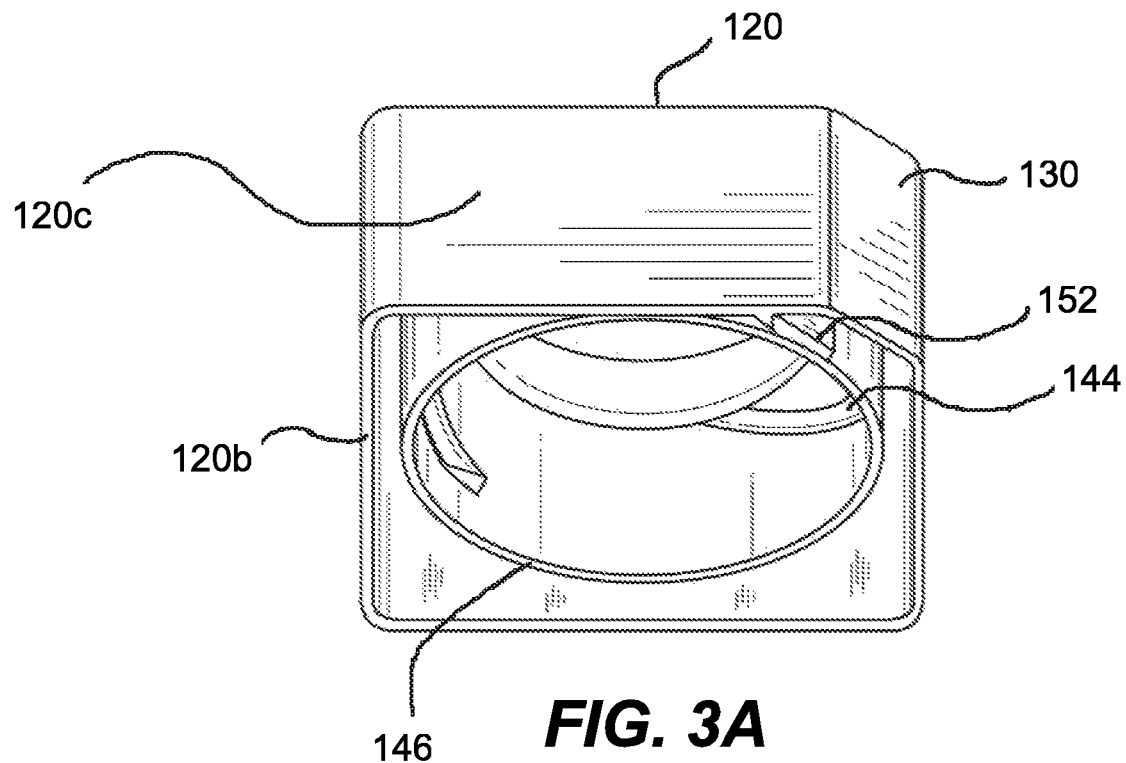
FIGS. 3A-3B illustrate bottom front and right perspective views of a cap according to embodiments.
Figure 3B:
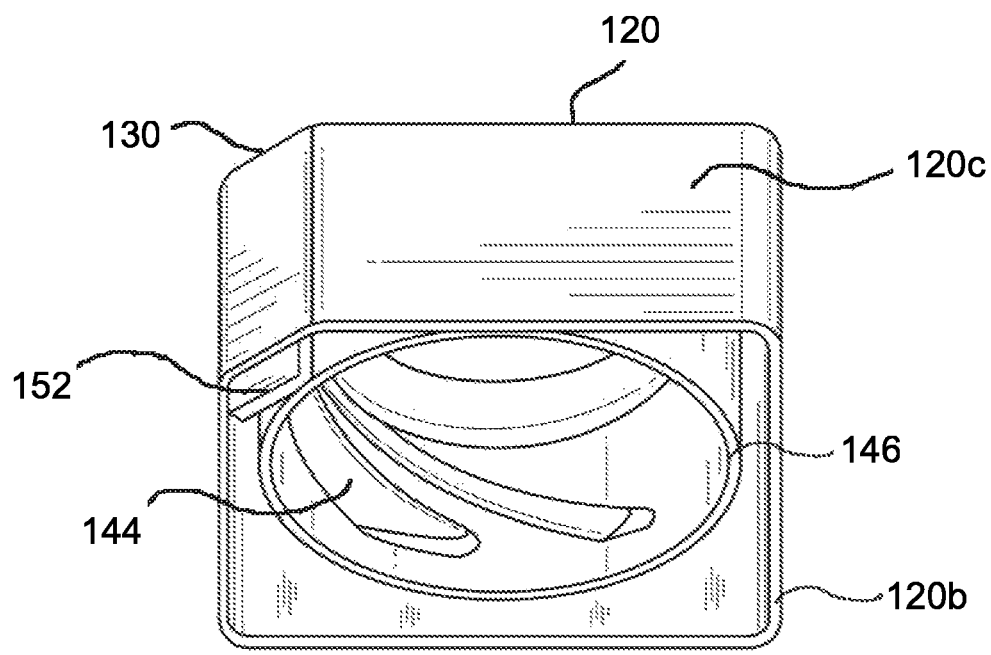

In certain embodiments, non-uniform spacing of the thread configuration may prevent the closure from being cross-threaded, preventing the threads from engaging in the wrong location or position. By way of example, as shown in FIGS. 3A-3B, three non-uniformly spaced threads may be incorporated to ensure proper functioning. The shape of the thread "bottoms" at the thread lead-in may be flat so that the thread, while disengaged, will ride around the ledge on the bottle finish until the proper thread engagement is aligned. The size and spacing may be used to ensure that the closure is stable prior to engagement and to prevent improper engagement and cross-threading.

Generally, with reference to FIGS. 1, 2, 3A and 3B, the hollow body 110 includes a top portion 110a, a bottom portion 110b and side portions 110c extending between the top and bottom portion to enclose the hollow body. The top portion 110a of the hollow body further includes a neck 140 having threads 142, and the side portions 110c of the hollow body 110 are configured such that one or more corners, edges, or select portions of the cross-sectional form is optionally cut-off at an angle to create one or more longitudinal flat portion(s) 130. The cap 120 generally includes a top portion 120a, a bottom portion 120b and side portions 120c extending between the top and bottom portions, and configured so as to correspond in shape with the hollow body. The cap 120 includes a socket 146 having threads 144 generally corresponding to the threads 142 of the neck 140 of the hollow body 110 so as to engage and secure closure of the cap 120 to the neck 140. The hollow body 110 and the cap 120 further include interlocking tab portions 150, 152 to provide a child resistant closure mechanism.

In another aspect, a specialized information label is provided. In certain embodiments, the specialized information label of the invention may be secured to the hollow body described herein. The specialized label is generally designed to make it easier for a consumer to understand product information, contents, ingredients, administration instructions, warnings, etc. The specialized label may be configured in any suitable manner so as to accommodate a desired product container. For instance, the specialized information label systems described herein may be used in connection with any suitable consumer product container, e.g., re-usable water or drink bottle, food container, drink container, etc. As will be recognized, the specialized information label systems of the invention may be used to provide required labeling, contents, ingredients, instructions, warnings, etc., for any consumer product, and can be configured to accommodate any consumer product packaging.

More particularly, in certain embodiments, the specialized information label may be configured to accommodate a hollow body of a product container described herein. In certain embodiments, the specialized information label may include multiple panels sufficient in number to align with surfaces of the hollow body. In certain embodiments, the label may wrap around only a portion of the hollow body (plus the Flat(s)), leaving the remaining side or portion unlabeled, to thereby leave a side or portion of the hollow body available for viewing of the contents of the hollow body (e.g., contents, pills or liquid remaining in the container).

As depicted in FIG. 4 and explained in further detail herein, in one embodiment, the label may have multiple panels secured to the hollow body of the product container, e.g., three and one quarter outer panels (not shown, see FIG. 5A), two inner panels 410a and an expandable feature 410b to store additional information on the reverse, or inside, side.

As shown in FIGS. 5A-5B, in one embodiment of the invention, a specialized label (not secured to a hollow body) is illustrated, wherein the first outer panel 510a may list product information, such as drug, pharmacy and patient information. A second outer panel 510b may list detailed product information, including dosing instructions and primary warnings associated with taking the medication. A third outer panel 510c may show visual, pictorial administration instructions, e.g., a MedChart. The third outer panel 510c may also include the first name of the consumer/patient in large, bold type. This feature allows the consumer to immediately recognize which medications belong to him or her.

Figure 9:
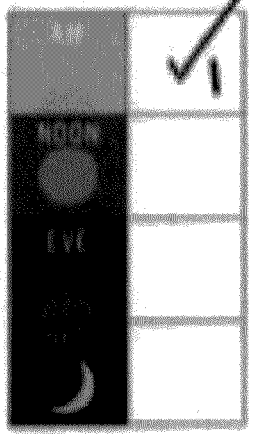
FIG. 9 depicts an exemplary prescriber pad according to the present embodiment.
Figure 14A:
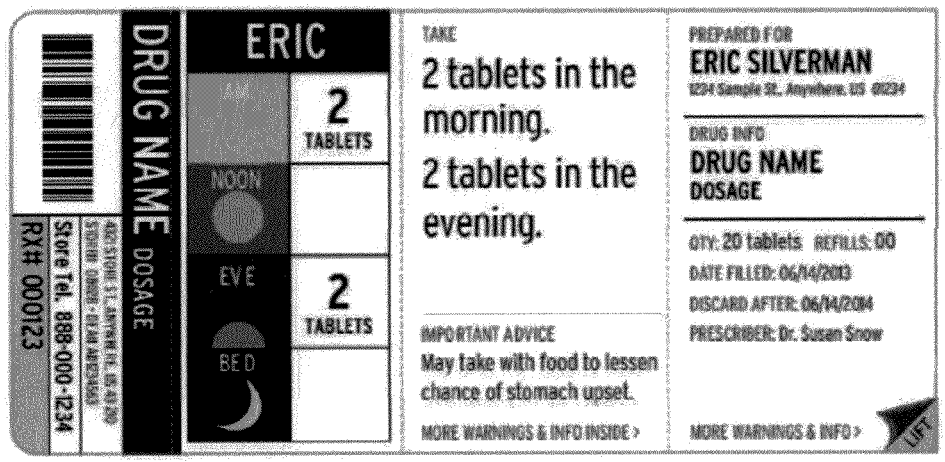
FIGS. 14A-14C illustrate front views of labels detached from a product container and folded out having different, exemplary MedCharts.
Figure 14B:
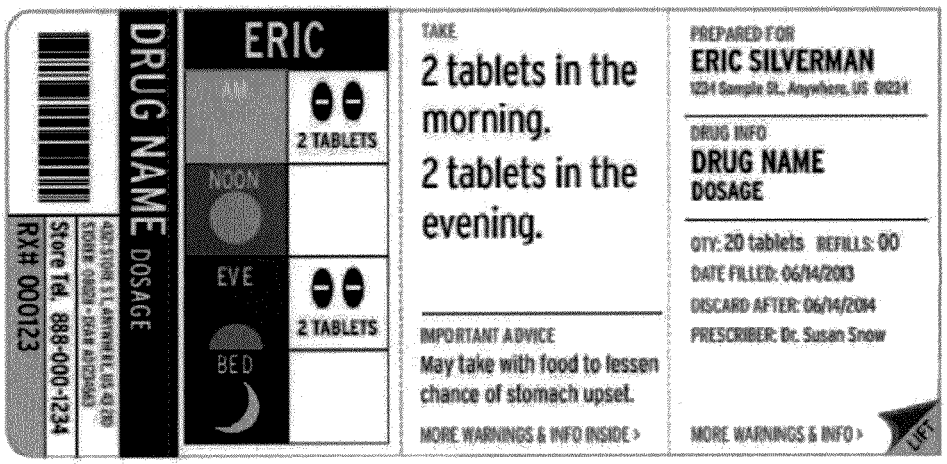
Figure 14C:
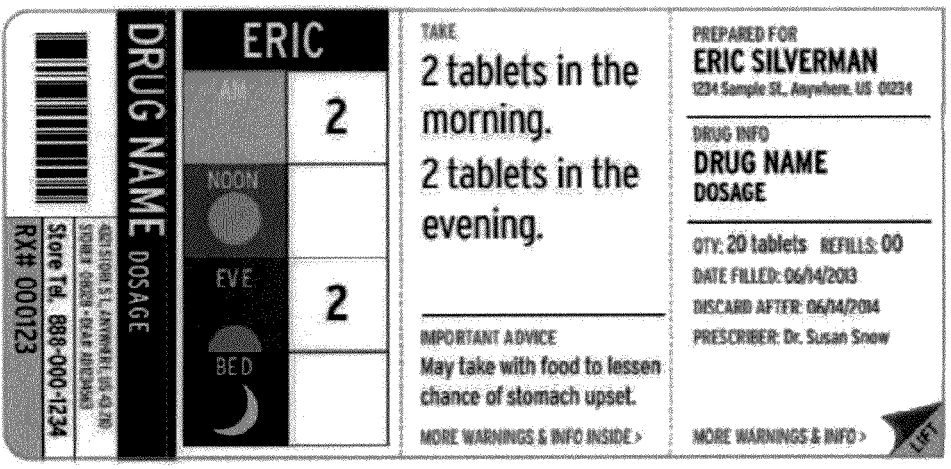

In certain embodiments, the MedChart may have two or more vertical columns or multiple divided areas (e.g., horizontal divided areas, diagonal, etc.), separated into multiple rows or subareas. In the first column or divided area, an icon or pictorial representation may be listed in each corresponding row or subarea for a medication administration timeframe, such as morning, noon, evening, bed time, meal time (breakfast, lunch, dinner, snack time), etc. The second column or divided area may call out (e.g., through pictorial representation), in the corresponding row or subarea, the amount of medication to be taken during that particular time frame. FIGS. 14A-14C depict exemplary embodiments of such MedCharts. For example, as shown on FIG. 14B, this portion of the MedChart might show a picture of two tablets. In another embodiment, as shown on FIG. 14C, this portion of the MedChart might show a very large "2", indicating two tablets should be taken in the morning and again in the evening. This MedChart provides several benefits to the consumer. First, it is a quick iconic reference for someone to see their exact dosage during the correct time frame. It is also beneficial for people who do not read English well. Third, if the consumer arranges multiple bottles with the MedChart facing outwards, it is possible to see at a glance when multiple medications must be taken. In certain aspects, prescriber pads could be integrated with the MedChart, wherein the prescriber provides clear information to the pharmacist/dispenser in a format similar to the MedChart regarding dosage administration in the appropriate time frame, e.g., AM, Noon, Eve, Bed, meal time, etc. FIG. 9 depicts an exemplary prescriber pad according to the present embodiment. In another embodiment, prescriber information may be provided through an electronic medical record (EMR).

A fourth outer panel 510d may, e.g., include the name of the medication in large, bold type, as well as measurement markers for liquid medications. This feature allows an individual to immediately determine the contents of the bottle. The fourth outer panel, in certain embodiments, may be configured to be aligned with the Flat 130 of the hollow body upon securing to the pharmaceutical container.

An expandable feature of the label 510e, configured to fold out from the hollow body upon securing to a container, e.g., a pharmaceutical container (see, e.g., FIG. 4, 410b) provides for one or more inner panels, 510e-1, 510e-2, that can include useful information, e.g., for user administration, medicament usage and warnings, etc.

With reference to FIG. 5B, in one embodiment, the specialized label may optionally be printed in a double-sided manner. More particularly, as shown, the specialized label may be printed double-sided to provide for the outer panels and inner panels, and configured so as to fold along desired fold lines to provide the expandable feature and secure to the product container. By way of example, first 512a and second 512b inner panels may display relevant advice and secondary precautions for, e.g., the prescribed medication. If desired (depending on the size of the expandable feature), third and fourth inner panels may display, e.g., patient information, drug information, common uses of the medication, pharmacy information and provider information. The patient and drug information can be repeated on inner and outer panels so it is always visible.

Figure 10A:
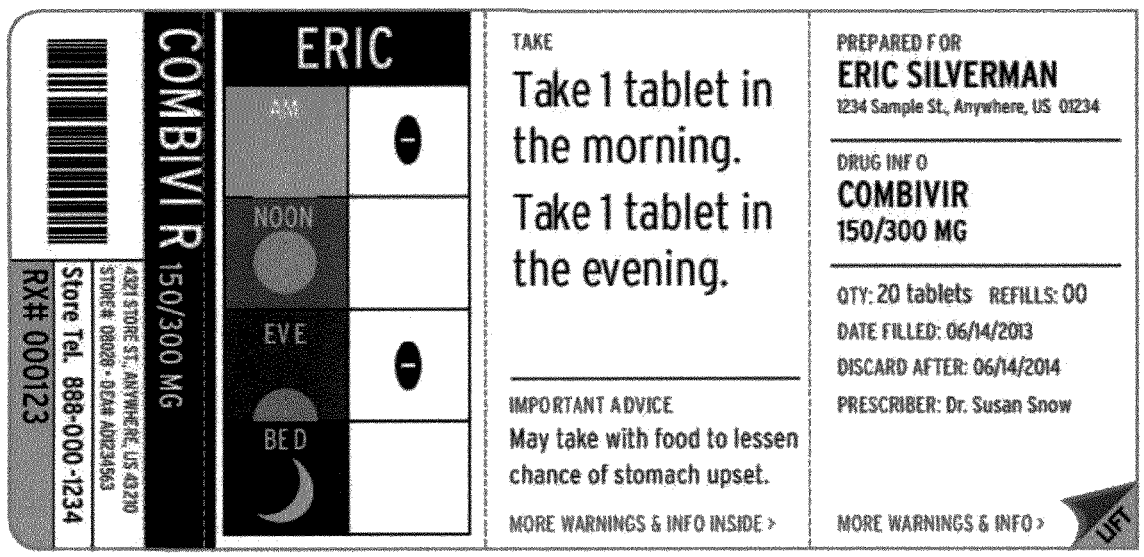
FIGS. 10A-10B illustrate front and rear views of a label detached from a product container and folded out according to embodiments.
Figure 10B:
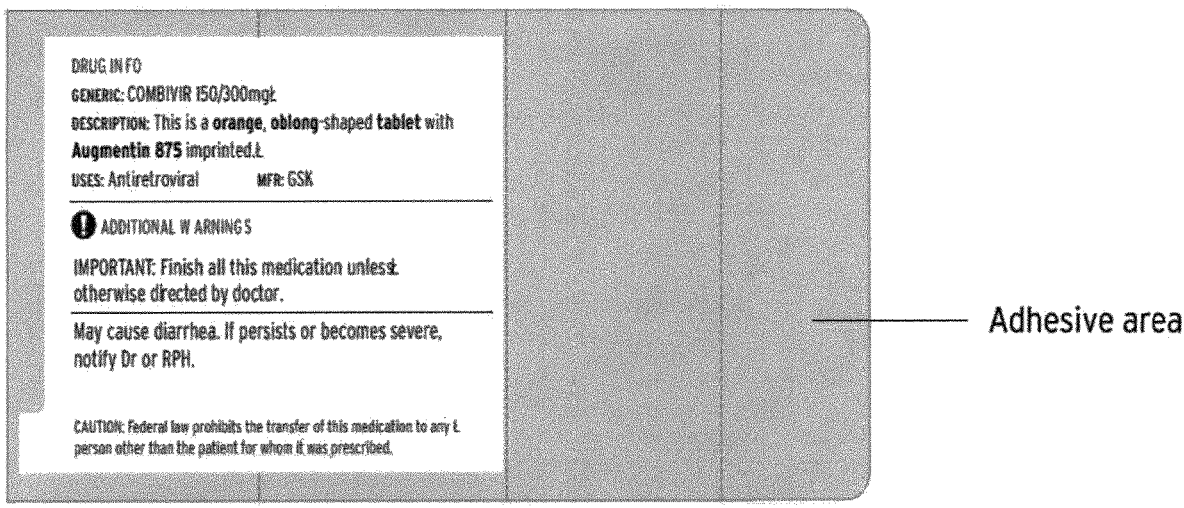
Figure 11A:
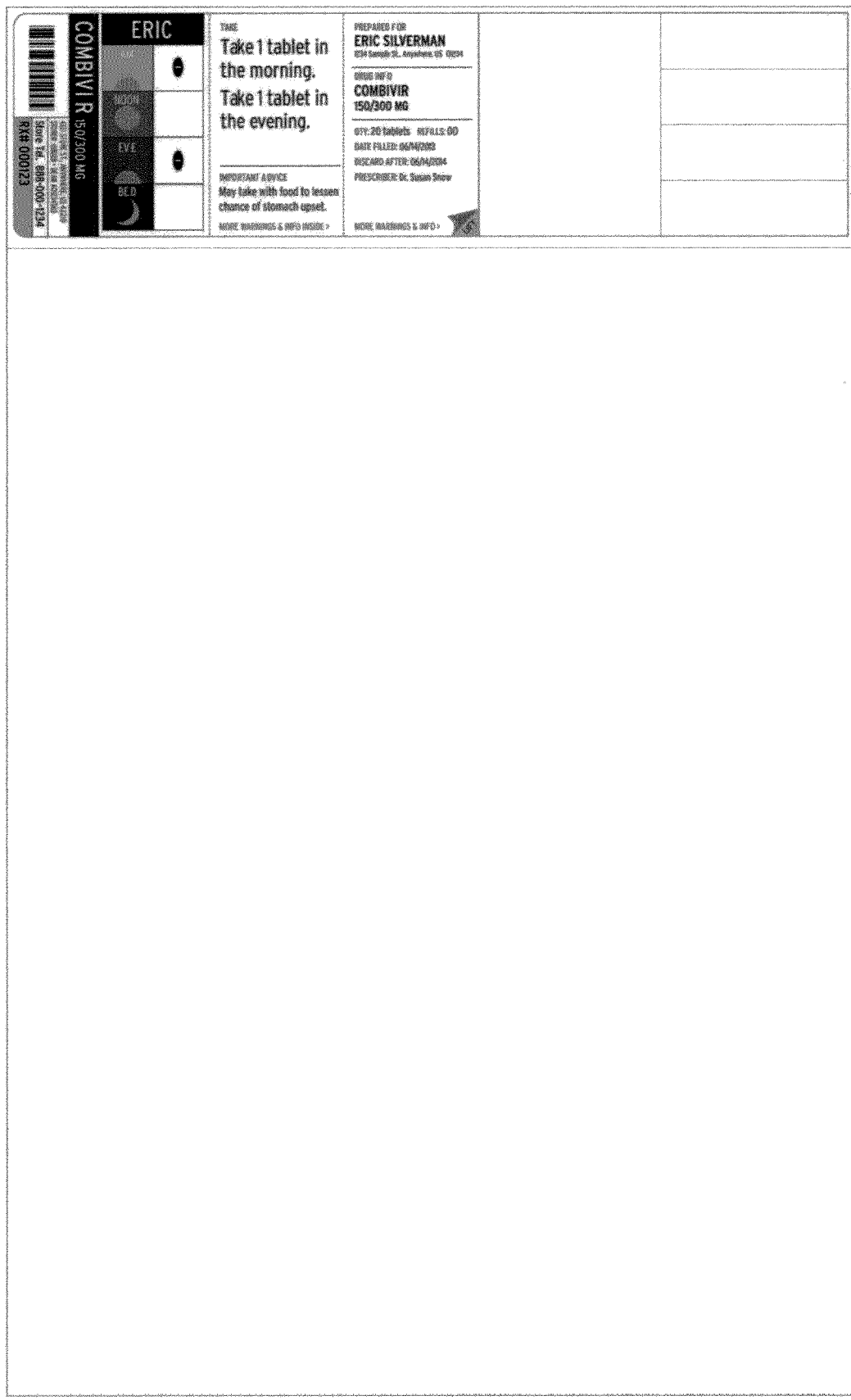
FIGS. 11A-11B illustrate front and rear views of an exemplary printer sheet of labels.
Figure 11B:
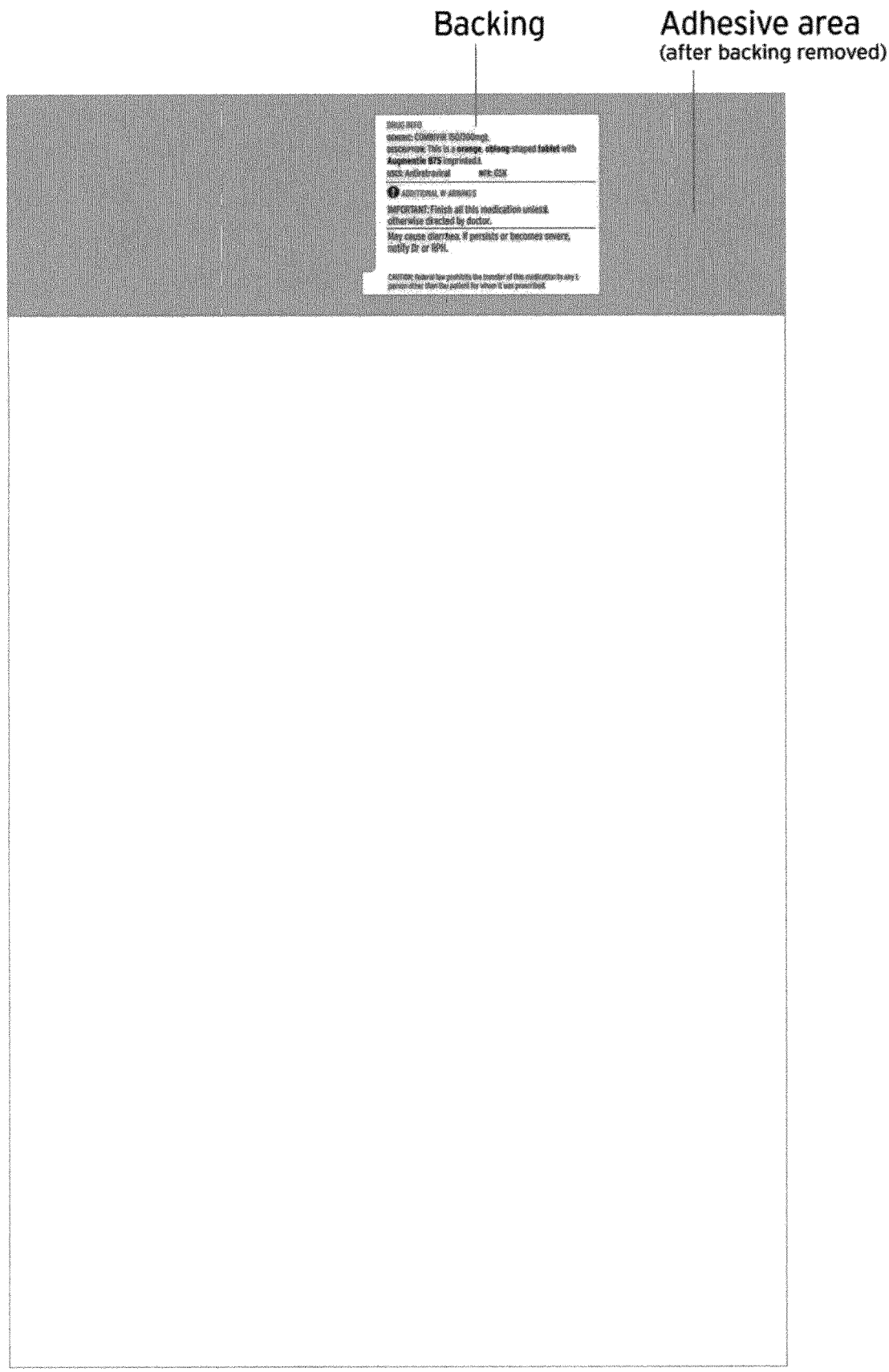

FIGS. 10A-10B illustrate an exemplary specialized label printed in a double-sided manner. More particularly, as shown, the specialized label may be printed double-sided to provide for outer panels and inner panels, and configured so as to fold along desired fold lines to provide the expandable feature and secure to the product container. By way of example, FIG. 10A illustrates exemplary outer panels; a first outer panel 1010a may list primary product information, e.g., drug, pharmacy and patient information. A second outer panel 1010b may show visual, pictorial administration instructions, e.g., a MedChart as described above. Third and fourth outer panels 1010c and 1010d may also include useful information regarding the product, e.g., product quantity and the date the product was prepared. These panels may be releasable from the product container such that, as shown on FIG. 10B, the reverse side of these panels 1010c and 1010d may contain further useful information, e.g., for user administration, usage and warnings. FIGS. 11A and 11B illustrate one example of how such a label might be printed on an 8×14" label sheet.

Figure 12A:
FIGS. 12A-12B illustrate full views of a label attached to a product container having a square cross-section and a flat according to an embodiment.
Figure 12B:
Figure 13A:
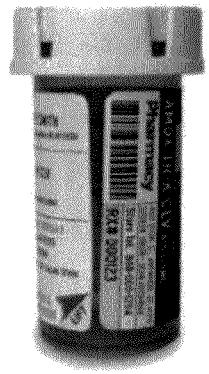
FIGS. 13A-13E illustrate full views of a label attached to a product container having a round cross-section according to an embodiment.
Figure 13B:
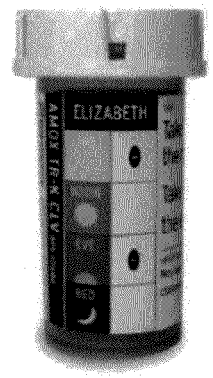
Figure 13C:
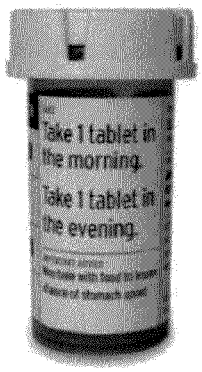
Figure 13D:
Figure 13E:

FIGS. 12A-12B depict one example of how a label, e.g. as shown on FIGS. 10A-10B, may be affixed to a product container having a square cross-section with a flat. FIG. 12A shows a product container with expandable panels 1010c and 1010d secured to the product container, while FIG. 12B shows a product container with expandable feature panels 1010c and 1010d detached and expanded from the product container. FIGS. 13A-13E illustrate how a double-sided label, such as the exemplary label shown on FIGS. 10A-10B, may be affixed to a product container having a round cross-section. FIGS. 13A-13D show alternative views of the product container having the label fully secured, while FIG. 13E shows the label with a panel expanded.

Figure 6:
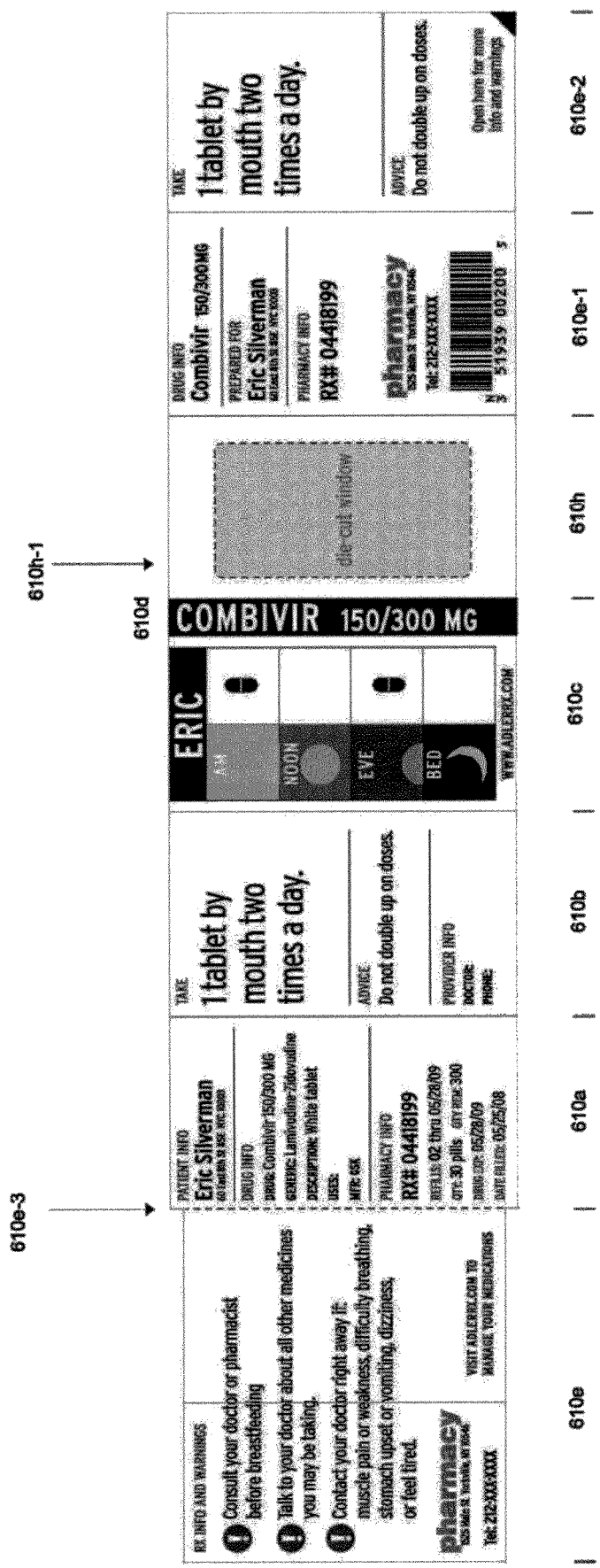
FIG. 6 illustrates a front view of an alternative label detached from a product container and folded out according to an embodiment.

In an alternative embodiment, e.g., as illustrated in FIG. 6, a single-sided specialized label may be desired (e.g., printed on a single side). In the embodiment shown, a first outer panel 610a may list product information, e.g., drug information, supplier information, pharmacy information, patient information, etc. A second outer panel 610b may list detailed product information, e.g., dosing instructions and primary warnings associated with taking the medication. A third outer panel 610c may show visual, pictorial administration instructions, e.g., a MedChart as described above. The third outer panel 610c may also include, e.g., the first name of the consumer/patient in large, bold type. This feature allows the consumer to immediately recognize which medications belong to him or her.

A fourth outer panel 610d may include, e.g., the name of the medication in large, bold type, as well as measurement markers for liquid medications. This feature allows an individual to immediately determine the contents of the bottle. The fourth outer panel, in certain embodiments, may be configured to be aligned with the Flat 130 of the hollow body upon securing to the pharmaceutical container.

An expandable feature of the label 610e, configured to fold out along 610e-3 from the hollow body upon securing to the pharmaceutical container (see, e.g., FIG. 4, 410b) provides for one or more inner panels, 610e-1, 610e-2, that can include useful information, e.g., for user administration, medicament usage and warnings, etc.

An optional feature may be included which allows for a clear view window, 610h. In certain embodiments, panel 610h may be configured with a die-cut window 610h-1 that may be removed prior to, upon application, or following application to a pharmaceutical container, to thereby allow visual access to the container.

In another embodiment, e.g., as illustrated in FIG. 7A, a single-sided specialized label may be desired with fewer panels, e.g., so as to better accommodate round containers or containers with fewer sides. As shown in FIG. 7A, a front view of a flat, open label is illustrated. A first outer panel 710a may list primary product information, e.g., drug, pharmacy and patient information. A second outer panel 710b may show visual, pictorial administration instructions, e.g., a MedChart as described above. If desired, a third outer panel 710c may also include the first name of the consumer/patient, the contents (e.g., medication), as well as measurement markers for liquids, in large, bold type. Alternatively, this information may be incorporated into the second outer panel (MedChart), if desired. This feature allows an individual to immediately determine the contents of the bottle. The third panel, in certain embodiments, may be configured to be aligned with the Flat 130 of the hollow body upon securing to the container.

An expandable feature of the label 710d, configured to fold along fold-lines 710e to provide for the expandable feature, may include one or more inner panels 710d-1, 710d-2 that can include useful information, e.g., for user administration, usage and warnings, etc. Upon folding, outer panel 710b releasably secures to outer panel 710a to conceal inner panels 710d-1 and 710d-2 within expandable feature 710d. Upon folding out of the label, inner panels 710d-1 and 710d-2 may then be viewed.

Figure 7B:
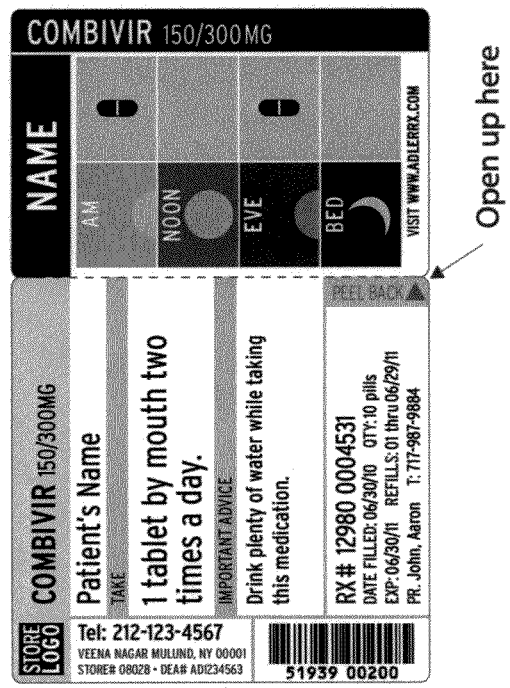
Figure 7C:
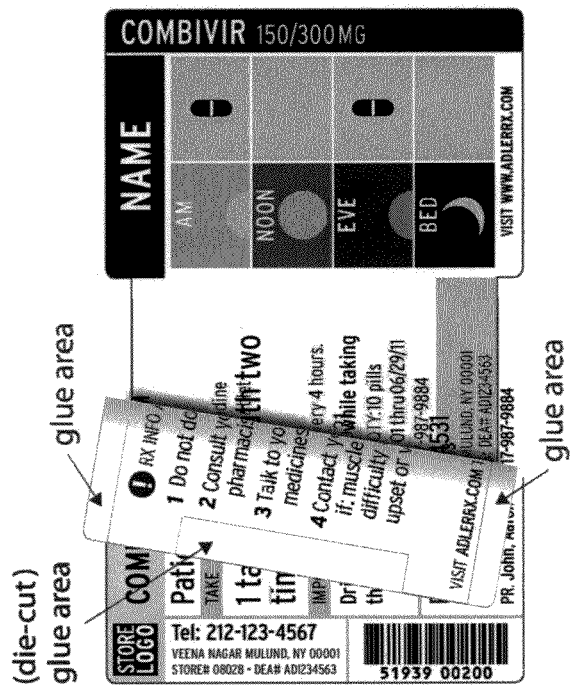
Figure 7D:
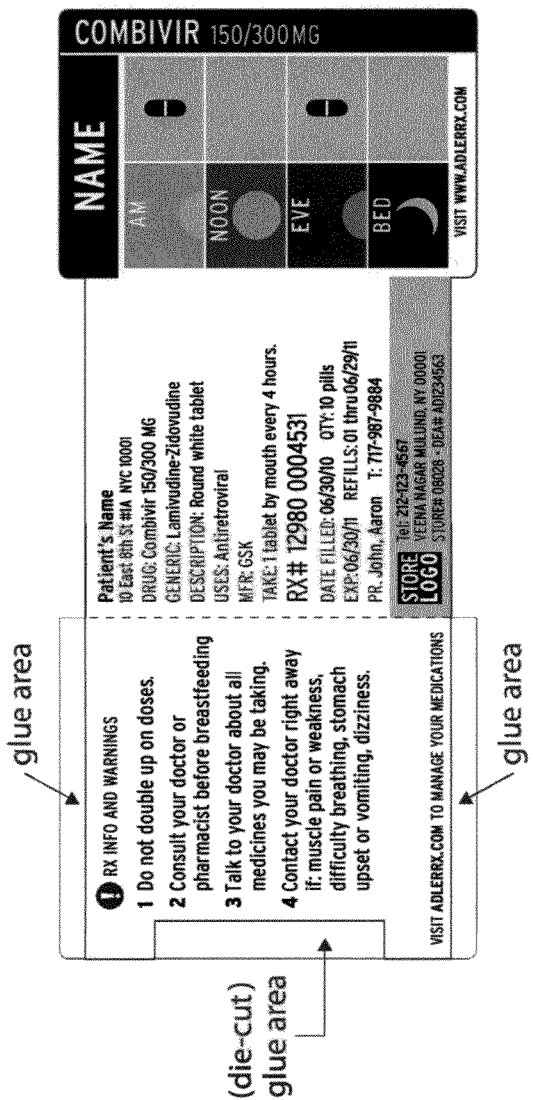
Figure 7E:
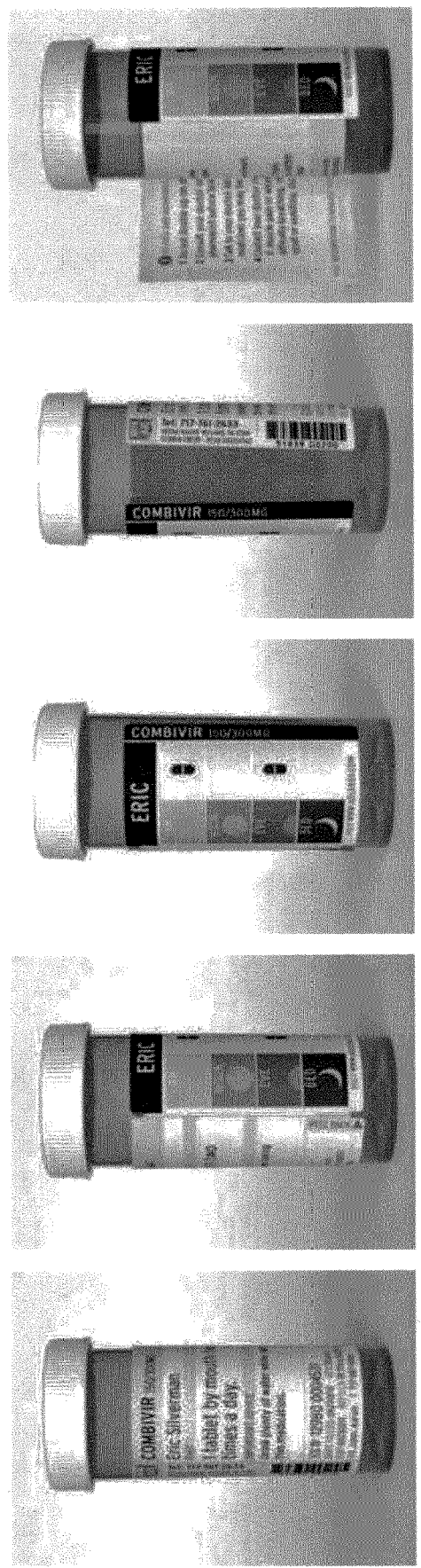

Additional views of the label shown in FIG. 7A are shown in FIGS. 7B-7E to illustrate wherein the expandable feature is in a folded-in configuration (e.g., FIG. 7B), partially folded-out to partially show the inner panels (e.g., FIG. 7C), folded-out to fully show the inner panels (e.g., FIG. 7D), and exemplary embodiments wherein the label is affixed to rounded containers and in a closed configuration (e.g., FIG. 7E).

Figure 15A:
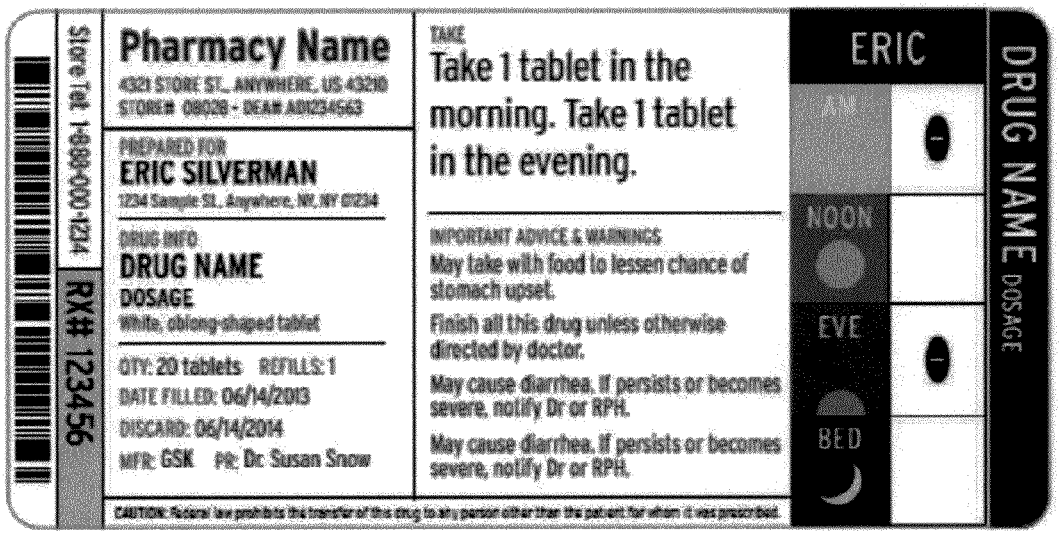
FIGS. 15A-15B illustrate front views of labels detached from a product container according to embodiments.
Figure 15B:
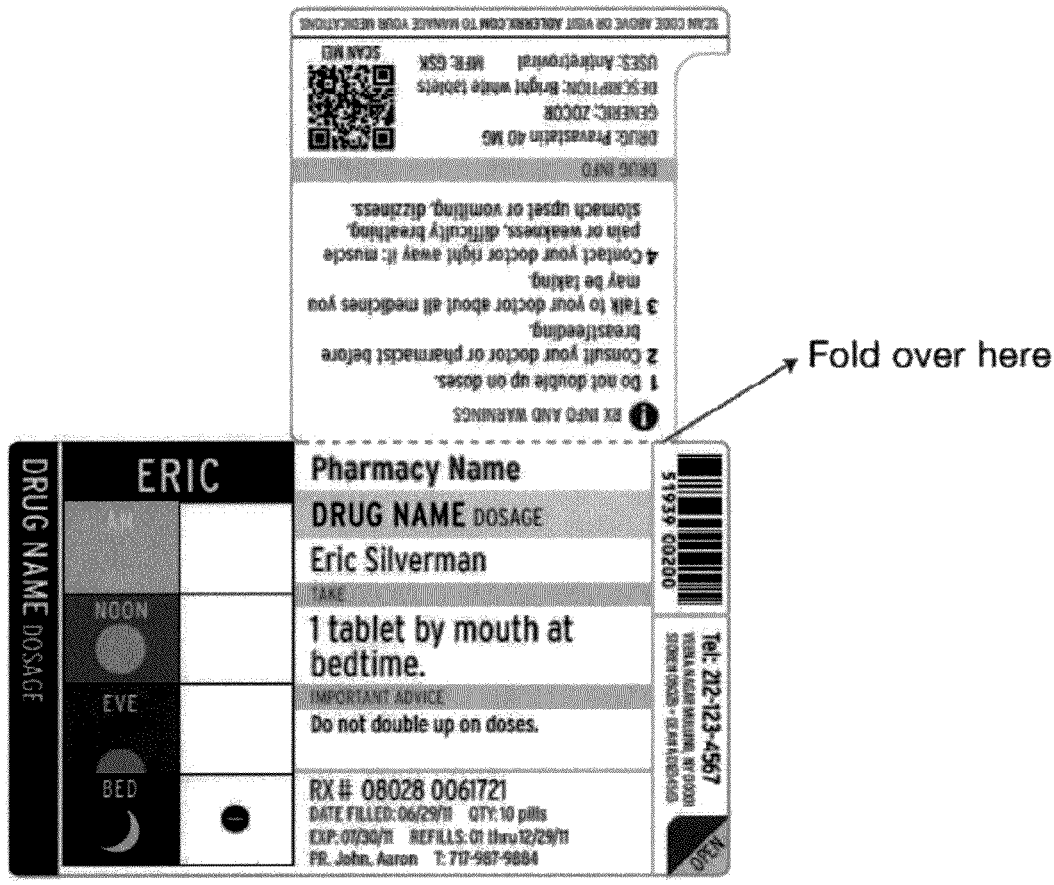

FIGS. 15A and 15B show other exemplary embodiments of a single-sided specialized label. In the embodiment shown on FIG. 15A, a first outer panel may list primary product information, e.g., drug, pharmacy and patient information. A second outer panel may show visual, pictorial administration instructions, e.g., a MedChart as described above. In the exemplary embodiment shown on FIG. 15A, there may not be an expandable feature. Alternatively, in the exemplary embodiment shown on FIG. 15B, an expandable feature may fold out along the top of the label. It will be understood that the pictured embodiments are merely exemplary and portions of the label also, or alternatively, may fold out along the side of the label and/or the bottom of the label.

The containers described herein provide a variety of benefits. Without intending to be limited, in certain embodiments, storing the bottles is simple: all bottles can be organized with the "front" facing outwards, so that relevant information is easily legible. This is convenient both for pharmacists and consumers. The configuration and sizing allows for more information to be conveyed on the specialized label. Further, the configuration and shape may improve ease of use. For example, child-resistant caps on medication bottles are usually troublesome to push and twist even for the most skilled set of hands. The unique shape of the container, combined with the novel form of child resistant cap, provides an additional point of leverage making the container easy to grip and open. In certain embodiments, the Flat may provide a convenient surface on the closure for a thumb or finger while pressing inward to release the child-resistant tab from the latch on the bottle.

In yet another aspect, a specialized label incorporating a MedChart may link users (e.g., pharmacists, prescribers, patients, etc.) to an interactive medication management system where users can get assistance in monitoring medications, dosing regimens, as well as accurately track current and past medications. In certain embodiments, the interactive medication management system may be a stand-alone computer system, a networked computer system, an on-line computer system, a website, etc.

In certain embodiments, the MedChart of the specialized label may be replicated on and linked to the interactive medication management system. By way of example, the specialized label may include information which directs patients to a website, where patients may view information concerning medication related to the MedChart, input additional medication information, organize and keep track of their medications, as well as share their information with other authorized users, including authorized family members, authorized prescribers, authorized pharmacists, etc. Further, the website may connect the patient with his or her prescribers, dispensers, and other health professionals to improve communication across these lines of health care, assuring proper understanding around medication regimens and promoting adherence.

Figure 8B:
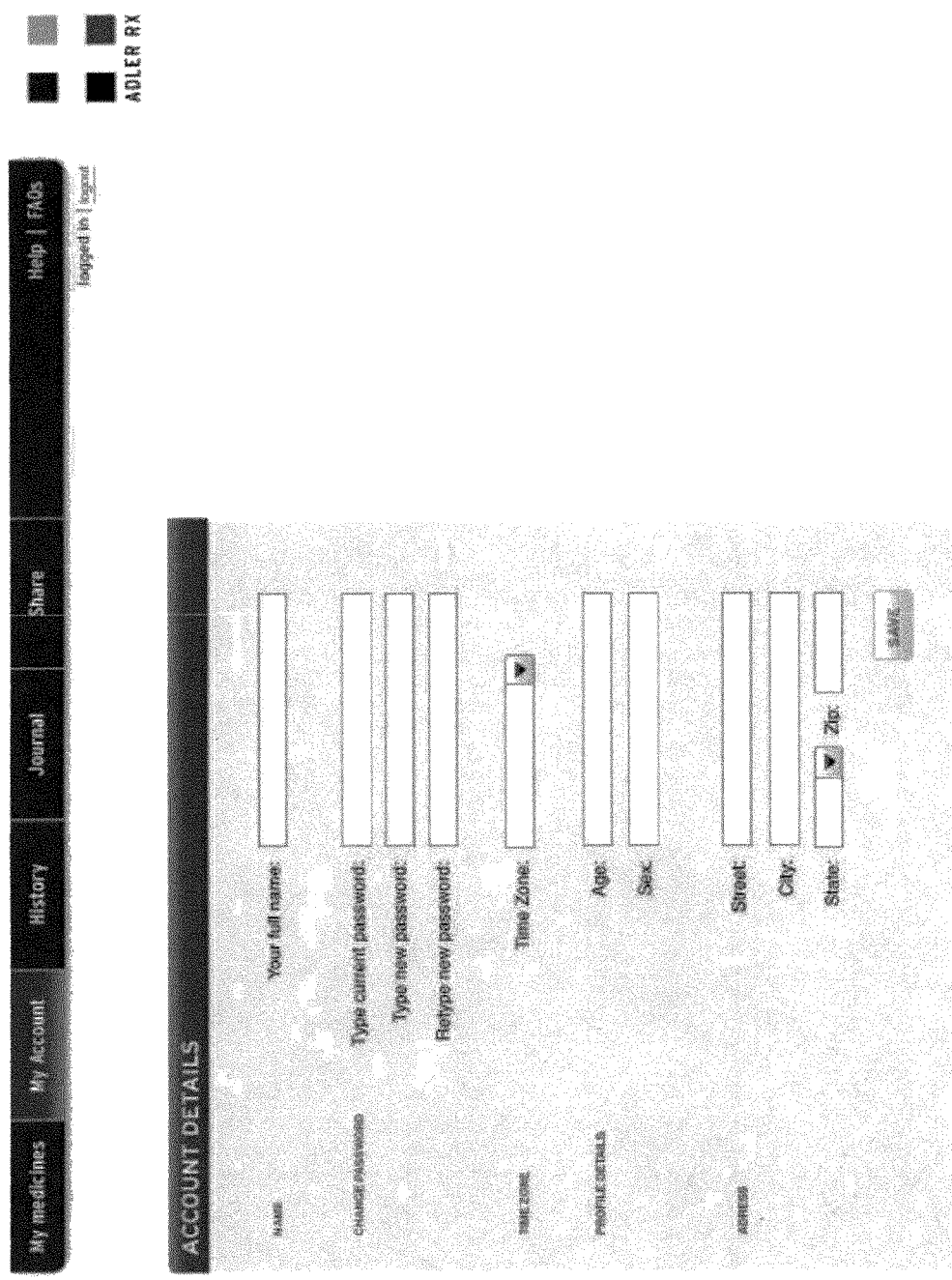
Figure 8D:
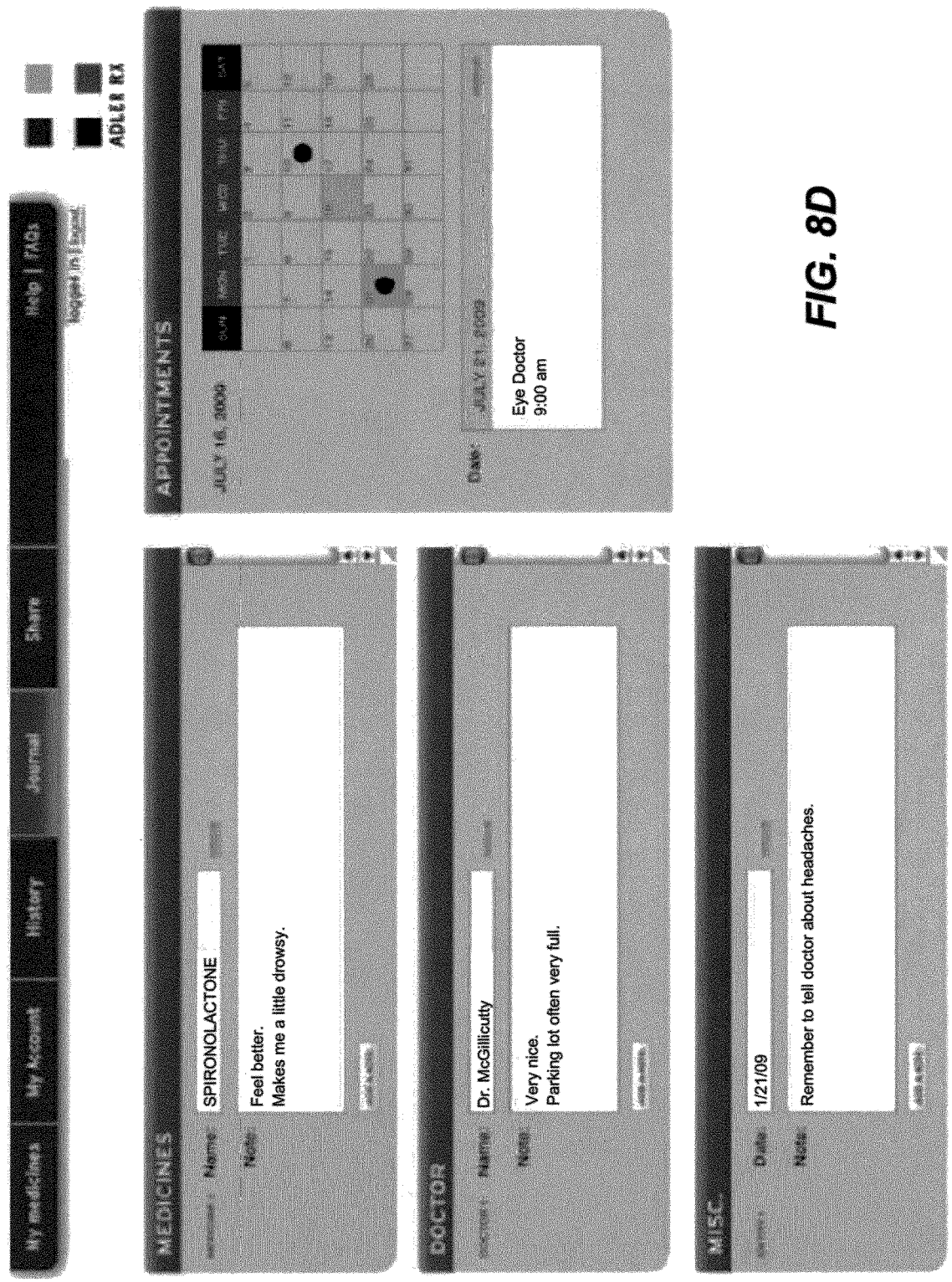
Figure 8G:
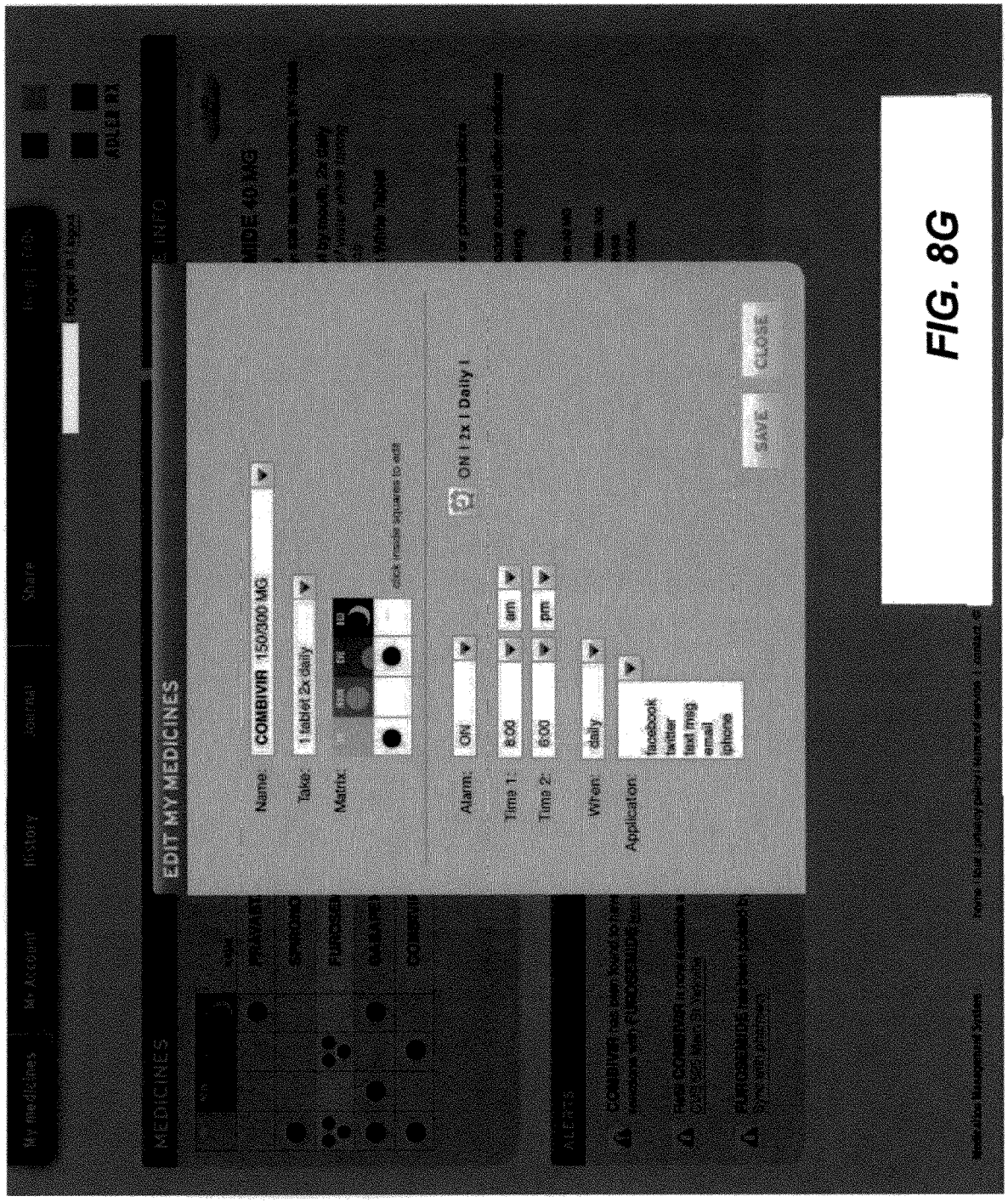

In one embodiment of the invention, the interactive medication management system may include one or more of the following types of interactive online content:

a "home" page providing an overview of the medication management system (see FIG. 8A);

a "tour" page providing a more comprehensive explanation of how the interactive management system works (not shown);

an encrypted registration page and portal for consumers to enter their 1) personal health history, 2) daily/weekly/monthly medication regimen, and 3) provider profiles (pharmacy, physicians). "Sign up" may, in some embodiments, be driven by the pharmacy or the physician (see FIGS. 8B-8D);

a resources page to direct patients to useful web links and local community resources (not shown); a "medical organizer" page which pulls together all pertinent information and displays any necessary alerts, such as "Your medication X has been recalled," or "You have a prescription ready at the pharmacy." This page may also provide options for adding and organizing medications (both over-the-counter and prescription) and user preferences, such as alert notifications (see FIGS. 8E-8F);

a "medical reminder" page, which provides adherence support to consumers by providing options for consumers to receive electronic reminders to take medicine, order a refill, or go to a medical appointment via social networking sites (such as Facebook, MySpace, Twitter, etc.) or via email, SMS, text, etc. (see FIG. 8G); and a "medical share" page, which provides an option to share personal medication information and communicate with pharmacists, health care providers, caregivers, and/or family members (see FIG. 8H).

By way of non-limiting example, an illustrative map of online content of an interactive medication management system is shown in FIG. 8I. As will be generally recognized by those of skill in the art, information for use in connection with the interactive medication management system may be stored in one or more database(s), displayed via one or more user interfaces, and communicated over any suitable technology (e.g., intranet, extranet, internet, cellular networks, etc). Data and information may be uploaded, stored, input, etc. into databases in any known manner, and interactive online content may be displayed in any known manner (websites, VPN networks, intranets, etc.).

The interactive medication management system may also provide an option for an on-line viewable and/or computer-printable pictorial management service. By way of example, the on-line viewable and/or computer-printable pictorial management service may provide an option to view and/or print dosing and/or appointment calendars, e.g., pocket calendars, desk calendars, etc., including daily, weekly, monthly, etc. dosing instructions (e.g., MedChart information), refill reminders, appointment reminders, etc.

The interactive medication management system provides numerous benefits for users, such as reducing the need for in-person or telephone interactions with medical providers, assisting the patient in adhering to a schedule, organizing medications, providing reminders, sharing information, and tracking side effects. The interactive system can also consolidate all of the patient's medications, whether over-the-counter or prescribed. It may generate a complete MedChart which gives a visual indicator of medication schedules and may be linked to the MedChart shown on each label. The interactive system may also provide for comprehensive information sharing; by patient invitation, the system may allow healthcare providers access to medical records and to be notified when the patient fills or refills a medication. It may also allow a patient to share information with family members or friends. The system may further provide links for medication information, such as medical references, the FDA website, or insurance education websites. It may also include a forum, where users can discuss health issues or consult with physicians or pharmacists about concerns.

The interactive system also provides benefits for physicians. The website provides a medication reconciliation tool, which serves as a master list of all medications taken by each patient, including over-the-counter medications and medications prescribed by other providers. This may prevent harmful interactions not caught at the pharmacy. The system also provides adherence follow-up information, such as a confirmation of whether the patient filled or refilled medications at the right times. It may assist in early intervention, by increasing communication and counseling with patients through a chat room or emailed questions.

The system further provides benefits for pharmacists and dispensers. It may serve as the "Medication Therapy Management" component under Medicare Part D, which allows pharmacies to include counseling over medications as part of the dispensing fee. The system may direct patient communication; if a patient is late on refills or if important updates are issues for a medication precaution, these issues are easy to address. The system may serve as a bridging function for medical and pharmacy technology. Further, the system may encourage efficiency, by allowing for easier and faster refill orders, and ensuring that these occur at the proper time by the ability to notify patients that they need to call in a refill, or even allow for an 'opt out' function.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims, in which all terms are meant in their broadest reasonable sense unless otherwise indicated therein.

What is claimed:

1. An interactive medication management system comprising:

a specialized information label configured to be affixed to a product container, wherein the specialized information label comprises medication identifying information and at least one information panel, wherein any one of the at least one information panels has visual, icon or pictorial administration instructions, and wherein the at least one information panel having visual, icon or pictorial administration instructions comprises:

an area separated into one or more subareas, each of the subareas including (i) an icon or pictorial representation indicating the timeframe in which a medication may be administered, wherein the icon or pictorial representation indicating the timeframe further comprises a numerical representation, an alphabetical representation, or a combination thereof, and (ii) a representation of the amount of medication to be taken during that particular timeframe, wherein the representation of the amount of medication is selected from the group consisting of an icon, a pictorial representation, a numerical representation, and a combination thereof;
a computerized database configured to store information from the specialized information label; and
a user interface coupled to the computerized database, wherein the user interface is configured to allow an individual to use a computing device to access and view at least a portion of the information stored within the computer database,
wherein the specialized information label when affixed to the product container is configured to display visual alignment of the amount of medication taken in each timeframe across a next specialized information label comprising different medication identifying information that is affixed to a next product container when the product container and the next product container are arranged facing outwards in the same direction, and wherein each timeframe is aligned horizontally or vertically.

2. The interactive medication management system of claim 1, wherein the user interface is a web-based portal.

3. The interactive medication management system of claim 1, wherein the user interface is a smartphone-based application.

4. The interactive medication management system of claim 1, wherein the user interface is further configured to present information stored within the computerized database in a MedChart format comprising an area separated into one or more subareas, each of the subareas including (i) an icon or pictorial representation indicating the timeframe in which a medication may be administered, wherein the icon or pictorial representation indicating the timeframe further comprises a numerical representation, an alphabetical representation, or a combination thereof, and (ii) a representation of the amount of medication to be taken during that particular timeframe, wherein the representation of the amount of medication is selected from the group consisting of an icon, a pictorial representation, a numerical representation, and a combination thereof.

5. The interactive medication management system of claim 1, wherein the computerized database is further configured to provide one or more alerts to a user.

6. The interactive management system of claim 5, wherein the alert is selected from the group consisting of a medication administration reminder, a medication refill order reminder, and a medical appointment reminder.

7. The interactive medication management system of claim 5, wherein the computerized database is further configured to transmit the alert electronically to a computing device.

8. The interactive medication management system of claim 1, wherein the user interface is configured so as to allow a user to print information stored within the computerized database.

9. The interactive medication management system of claim 8, wherein the user interface is configured so as to allow a user to print medication administration instructions in a MedChart format comprising an area separated into one or more subareas, each of the subareas including (i) an icon or pictorial representation indicating the timeframe in which a medication may be administered, wherein the icon or pictorial representation indicating the timeframe further comprises a numerical representation, an alphabetical representation, or a combination thereof, and (ii) a representation of the amount of medication to be taken during that particular timeframe, wherein the representation of the amount of medication is selected from the group consisting of an icon, a pictorial representation, a numerical representation, and a combination thereof.

10. The interactive medication management system of claim 8, wherein the user interface is configured so as to allow a user to print dosing calendars or appointment calendars.

11. The interactive medication management system of claim 1, wherein the specialized information label is single-sided or double-sided.

12. The interactive medication management system of claim 1, wherein the specialized information label further comprises a fold-out product information panel.

13. The interactive medication management system of claim 1, wherein the specialized information label includes one or more inner information panels configured to display information when a fold-out product information panel of the label is in a fold-out configuration.

14. The interactive medication management system of claim 1, further comprising electronic prescriber information having visual, icon or pictorial administration instructions, wherein the electronic prescriber information comprises an area separated into one or more subareas, each of the subareas including (i) an icon or pictorial representation indicating the timeframe in which a medication may be administered, wherein the icon or pictorial representation indicating the timeframe further comprises a numerical representation, an alphabetical representation, or a combination thereof, and (ii) a representation of the amount of medication to be taken during that particular timeframe, wherein the representation of the amount of medication is selected from the group consisting of an icon, a pictorial representation, a numerical representation, and a combination thereof.

15. The interactive medication management system of claim 14, wherein the electronic prescriber information is provided through an electronic medical record (EMR).

16. The interactive medication management system of claim 13, wherein the specialized information label further includes one or more outer panels configured to display information.

17. The interactive medication management system of claim 16, wherein at least two of the one or more outer panels are releasably secured to conceal said one or more inner panels.

18. The interactive medication management system of claim 12, wherein the fold-out information panel folds along a direction selected from the group consisting of top of the specialized information label, bottom of the specialized information label, and a side of the specialized information label.

19. The interactive medication management system of claim 1, wherein each of the representation of the amount of medication represents different medications.

20. The interactive medication management system of claim 4, wherein each of the representation of the amount of medication represents different medications.

21. The interactive medication management system of claim 9, wherein each of the representation of the amount of medication represents different medications.

22. The interactive medication management system of claim 14, wherein each of the representation of the amount of medication represents different medications.

23. The interactive medication management system of claim 1, wherein the representation of the amount of medication further comprises an alphabetical representation.

24. The interactive medication management system of claim 23, wherein the alphabetical representation is an abbreviation.

25. The interactive medication management system of claim 4, wherein the representation of the amount of medication further comprises an alphabetical representation.

26. The interactive medication management system of claim 25, wherein the alphabetical representation is an abbreviation.

27. The interactive medication management system of claim 9, wherein the representation of the amount of medication further comprises an alphabetical representation.

28. The interactive medication management system of claim 27, wherein the alphabetical representation is an abbreviation.

29. The interactive medication management system of claim 14, wherein the representation of the amount of medication further comprises an alphabetical representation.

30. The interactive medication management system of claim 29, wherein the alphabetical representation is an abbreviation.

\* \* \* \* \*